US009504735B2

(12) United States Patent
Sanders

(10) Patent No.: US 9,504,735 B2
(45) Date of Patent: Nov. 29, 2016

(54) CELL MEMBRANE TRANSLOCATION OF REGULATED SNARE INHIBITORS, COMPOSITIONS THEREFOR, AND METHODS FOR TREATMENT OF DISEASE

(76) Inventor: Ira Sanders, North Bergen, NJ (US)

(*) Notice: Subject to any disclaimer, the term of this patent is extended or adjusted under 35 U.S.C. 154(b) by 1202 days.

(21) Appl. No.: 12/940,826

(22) Filed: Nov. 5, 2010

(65) Prior Publication Data

US 2011/0054442 A1 Mar. 3, 2011

Related U.S. Application Data

(63) Continuation of application No. 10/545,872, filed as application No. PCT/US2004/005436 on Feb. 24, 2004, now abandoned.

(60) Provisional application No. 60/449,107, filed on Feb. 24, 2003.

(51) Int. Cl.
*A61K 38/00* (2006.01)
*A61K 38/48* (2006.01)

(52) U.S. Cl.
CPC ....... *A61K 38/4893* (2013.01); *A61K 38/4886* (2013.01)

(58) Field of Classification Search
None
See application file for complete search history.

(56) References Cited

U.S. PATENT DOCUMENTS

| | | | | |
|---|---|---|---|---|
| 4,876,194 | A | 10/1989 | Bjorck et al. | |
| 5,190,762 | A | 3/1993 | Yarosh | |
| 5,670,484 | A * | 9/1997 | Binder | 514/18.6 |
| 5,714,468 | A * | 2/1998 | Binder | 424/780 |
| 5,766,605 | A | 6/1998 | Sanders et al. | |
| 5,788,666 | A | 8/1998 | Atanasoska | |
| 5,976,542 | A | 11/1999 | Weiser et al. | |
| 5,989,545 | A | 11/1999 | Foster et al. | |
| 6,063,768 | A | 5/2000 | First | |
| 6,358,917 | B1 * | 3/2002 | Carruthers et al. | 424/780 |
| 6,429,189 | B1 | 8/2002 | Borodic | |
| 6,444,209 | B1 | 9/2002 | Johnson et al. | |
| 6,787,517 | B1 * | 9/2004 | Gil et al. | 514/1 |
| 7,655,244 | B2 | 2/2010 | Blumenfeld | |
| 7,749,515 | B2 | 7/2010 | Blumenfeld | |
| 8,530,425 | B2 | 9/2013 | Blumenfeld | |
| 2002/0086036 | A1 | 7/2002 | Walker | |
| 2002/0098236 | A1 | 7/2002 | Fischer et al. | |
| 2002/0127247 | A1 | 9/2002 | Steward et al. | |
| 2003/0027283 | A1 | 2/2003 | Bjorck et al. | |
| 2003/0059912 | A1 | 3/2003 | Bigalke | |
| 2003/0113349 | A1 | 6/2003 | Coleman | |
| 2003/0165541 | A1 | 9/2003 | Donovan | |
| 2004/0009180 | A1 | 1/2004 | Donovan | |
| 2004/0028706 | A1 | 2/2004 | Aoki et al. | |
| 2006/0153876 | A1 | 7/2006 | Sanders | |

FOREIGN PATENT DOCUMENTS

| | | |
|---|---|---|
| DE | 19852981 | 5/2000 |
| EP | 0163141 | 8/1991 |
| GB | 200118038 | 3/2001 |
| TW | 0017897 | 3/2000 |
| WO | 0028041 | 5/2000 |
| WO | 0200172 | 1/2002 |
| WO | 03101483 | 12/2003 |
| WO | 2004006954 | 1/2004 |

OTHER PUBLICATIONS (Carruthers et al Journal of the American Academy of Dermatology vol. 34 No. 5 Part 1 pp. 788-797).*

Palme r, et al., Induction Of BAIAP3 By The EWS-WTIchimeric Fusion Implicates Regulated Exocytosis In Tumorigenesis, Cancer Cell (2002) 6:497-505.

Panyam, et al., Rapid Endo-Lysosomal Escape Of Polydl-Lactide-Coglycolide Nanoparticles: Implications For Drug And Gene Delivery FASEB J. (2002) 16, 1217-1226.

Pooga et al., Cell Penetration By Transporatn FASEB J 1998, 12:67-77.

Raso, et al., Intracellular Targeting with Low pH-triggered Bispecific Antibodies Journal of Biological Chemistry, 1997, 272:27623-27628.

Rentel, et al., Niosomes As A Novel Peroral Vaccine Delivery Systemint. J. Pharm. Sep. 20, 1999;186(2):161-7.

Rossetto, et al., VAMP/Synaptobrevin isoforms 1 and 2 are widely and differentially expressed in non-neuronal tissues, J. Cell. Biol (1996) 132:167-79).

Schantz et al "Preparation and Characterization of Botulinum Toxin Type A for Human Treatment" (see pp. 42-45) (edited by Jankovic et al 1994 Therapy with Botulinum Toxin).

Schoch, et al., SNARE Function Analyzed in SynaptobrevinNAMP Knockout MiceScience (2001), vol. 294.

Sciarra, Aerosols2 Remington: The Science and Practice of Pharmacy 1676-1692, Alfonso R. Gennaro ed., 19th ed., 1995.

Sun, et al., Hrs regulates early endosome fusion by inhibiting formation of an endosomal SNARE complex The Journal of Cell Biology (2003) 162:125-137.

Tamori, et al., Cleavage of vesicle-associated membrane protein (VAMP)-2 and cellubrevin on GLUT4 containing vesicles inhibits the translocation of GLUT4 in 3T3-L1 adipocytes, Biochem. Biophys. Res. Commun. Mar. 27, 1996; 220 (3): 740-5.

Vives, et al., A Truncated HIV-1 Tat Protein Basic Domain Rapidly Translocates Through The Plasma Membrane And Accumulates In The Cell Nucleus, J Biol Chem 1997, 272:16010-16017.

Washbourne, et al., Genetic Ablation Of The T-SNARE SNAP-25 Distinguishes Mechanisms Of Neuroexocytosis, Nature Neuroscience (2002) 5:19-26.

Weller, et al., Cooperative Action of the Light Chain of Tetanus Toxin and the Heavy Chain of Botulinum Toxin Type A on the Transmitter Release of Mammalian Motor EndplatesNeurosci. Letters (1991) 122: 132-134.

(Continued)

*Primary Examiner* — Patricia Duffy
(74) *Attorney, Agent, or Firm* — Wilson Sonsini Goodrich & Rosati

(57) ABSTRACT

Compositions and methods of modulating cellular function and treatment of disease in mammals comprising locally administering a regulated SNARE inhibitor and a translocating agent to the mammal. Regulated SNARE inhibitors include clostridial neurotoxins, tetanus neurotoxin and their free light chain portions and IgA protease. Translocating agents include acids, encapsulating vectors, and transduction domains.

15 Claims, No Drawings

(56) References Cited

OTHER PUBLICATIONS

Weller, U., et al., "Chains and Fragments of Tetanus Toxin: Separation, Reassociation and Pharmacological Properties," European Journal of Biochemistry, vol. 182, 1989, p. 649-656.
Williamson, et al. Botulinum Neurotoxin C Acts On Syntaxin And Snap-25 And Is Cytotoxic To NeuronsMol. Biol. Cell 6:61a, 1995.
Williamson, et al., Clostridial neurotoxins and Substrate Proteolysis in Intact Neurons,J. Biol. Chem. 271:7694-7699, 1996.
Williamson, et al., Syntaxin and 25-kDa synaptosomal-associated protein: Differential effects of botulinumneurotoxins C1 and A on neuronal survival; J Neurosci Res 52:569-583 (1998).
Aoshiba, K., Alveolar Wall Apoptosis Causes Lung Destruction and Emphysematous Changes, American Journal of Respiratory Cell and Molecular Biology, vol. 28, pp. 555-562, 2003.
Gennaro, Alfonso R., The Science and Practice of Pharmacy, 19th ed., pp. 866-885, 1495-1523, 1524-1548, 1598-1614, 1676-1692 (1995).
U.S. Appl. No. 10/545,872 (US 2006-0153876) OA dated Restriction Requirement dated Jan. 11, 2008.
U.S. Appl. No. 10/545,872 (US 2006-0153876) Response/Restriction Requirement dated Feb. 11, 2008.
U.S. Appl. No. 10/545,872 (US 2006-0153876) Non-Final Rejection dated Jun. 11, 2008.
U.S. Appl. No. 10/545,872 (US 2006-0153876) Response/Amendment dated Sep. 11, 2008.
U.S. Appl. No. 10/545,872 (US 2006-0153876) Final Rejection dated Jan. 13, 2009.
U.S. Appl. No. 10/545,872 (US 2006-0153876) Response/Amendment dated Jul. 13, 2009.
U.S. Appl. No. 10/545,872 (US 2006-0153876) Non-Final Rejection dated Sep. 16, 2009.
U.S. Appl. No. 10/545,872 (US 2006-0153876) Response/Amendment dated Dec. 16, 2009.
U.S. Appl. No. 10/545,872 (US 2006-0153876) Final Rejection dated Mar. 30, 2010.
U.S. Appl. No. 10/545,872 (US 2006-0153876) Response/Amendment After Final dated Jul. 27, 2010.
U.S. Appl. No. 10/545,872 (US 2006-0153876) Advisory Action dated Aug. 17, 2010.
U.S. Appl. No. 10/545,872 (US 2006-0153876) Response/Amendment after Notice of Appeal dated Oct. 18, 2010.
U.S. Appl. No. 10/545,872 (US 2006-0153876) Response/Amendment after Notice of Appeal dated Oct. 29, 2010.
U.S. Appl. No. 10/545,872 (US 2006-0153876) Non-Final Rejection dated Dec. 9, 2010.
U.S. Appl. No. 10/545,872 (US 2006-0153876) Response/Amendment dated Mar. 9, 2011.
U.S. Appl. No. 10/545,872 (US 2006-0153876) Final Rejection dated Jun. 24, 2011.
International Search Report, International Preliminary Report on Patentability and Written Opinion for International Patent Application No. PCT/US2004/05436 issued Mar. 15, 2005.
European Search Report for European Patent Application No. 04714146.0 issued Jun. 15, 2009.
de Paiva, et al., "Light Chain Of Botulinum Neurotoxin Is Active In Mammalian Motor Nerve Terminals When Delivered Via Liposomes," FEBS Lett., 17; vol. 277, No. 1-2, pp. 171-174 (Dec. 1990).
Fu et al., "Spectroscopic Analysis of Low pH and Lipid-induced Structural Changes in Type A Botulinum Neurotoxin Relevant to Membrane Channel Formation and Translocation," Biophysical Chemistry, vol. 99, No. 1, pp. 17-29 (Sep. 3, 2002).
Qa'Dan, M., et al., "pH-Enhanced Cytopathic Effects of Clostridium Sordellii Lethal Toxin," Infection and Immunity, vol. 69, No. 9, p. 5487-5493 (Sep. 2001).
Apland, et al., Inhibition of Neurotransmitter Release by peptides that Mimic the N-Terminal Domina of SNAP-25, J. Protein Chem. (2003) 22:147-53).
Avis, et al., Parenteral Preparations2 Remington: The Science and Practice of Pharmacy 1524-1548, Alfonso R. Gennaro ed., 19th ed., 1995.
Ballestrasse, et al., Calculations of the pH changes produced in body tissue by a spherical stimulation electrode, Annals of Biomedical Engineering, (1985) 13:405-424.
Binder, et al., Botulinum toxin type A (Botox0) for the treatment of migraine headacheOtolaryngol Head and Neck Surg 123: 169-176.
Binscheck, et al., IgA protease from Neisseria gonorrhoeae inhibits exocytosis in bovine chromaffin cells like tetanus toxin,J. Biol. Chem . . . Jan. 27, 1995;270(4):1770-4.
Blersch, et al., Botulinum Toxin A And The Cutaneous Nociception In Humans: A Prospective, Double-Blind, Placebo-Controlled, Randomized StudyJ. Neurol. Sci., 205:59-63.
Blocker, D., et al., "Clostridium Botulinum C2 Toxin: Low pH-Induced pore formation is required for translocation of the Enzyme Component C21 into the Cytosol of Host Cells," The Journal of Biological Chemistry, vol. 278, No. 39, Sep. 26, 2003, p. 3736.
Bowie et al Science, 1990, 247:1306-1310.
Breedveld, Therapeutic monoclonal antibodies, Lancet 2000; 355: 735-40.
Burgess, et al., The Synaptic Protein Syntaxin 1 Is Required for Cellularization of *Drosophila* EmbryosThe Journal of Cell Biology, vol. 138, No. 4, Aug. 25, 1997 861-875.
Chan, et al., A Putative Link Between Exocytosis and Tumor DevelopmentCancer Cell (2002) 6:427-8.
Cheatham, et al., Insulin-stimulated translocation of GLUT4 glucose transporters requires SNARE-complexproteins, Proc. Natl. Acad. Sci. USA. Dec. 24, 1996; 93(26): 15169-73.
Conner, et al., Syntaxin Is Required for Cell Division Molecular Biology of the Cell, vol. 10, 2735-2743, Aug. 1999.
Cullen, Journey to the center of the cell. Cell 105, 697 (2001).
De Angelis, et al, Anti-GD1a antibodies from an acute motor axonal neuropathy patient selectively bind to motor nerve fiber nodes of Ranvier, 121 Journal of Neuroimmunology 79-82 (2001).
Diefenbach, et al., The Heavy Chain Of Conventional Kinesin Interacts With The Snare Proteins SNAP25 And SNAP23, Biochemistry 14906-14915 (2002).
Dressler, et al, Botulinum toxin type B for treatment of axillar hyperhidrosis J Neurol. Dec. 2002;249(12):1729-32.
Dreyer et al 1983 European Journal of Physiology vol. 399 pp. 228-234.
Dussor, et al., Cholinergic Modulation Of Nociceptive Responses In Vivo And Neuropeptide Release In Vitro At The Level Of The Primary Sensory Neuron, Pain 107 (2004) 22-32 ed., 19th ed., 1995.
Eleopra, et al., Botulinum neurotoxin serotype C: a novel effective botulinum toxin therapy in human. Neuroscience Letters 224 (1997) 91-94.
Eleopra, et al., Botulinum neurotoxin serotypes A and C do not affect motor units survival in humans: an electrophysiological study by motor units counting Clinical Neurophysiology 113 (2002) 1258-1264.
Fernandez-Salas, E., et al., "Is the Light Chain Subcellular Localization an Important Factor in Botulinum ToxinDuration of Action?", Movement Disorders, vol. 19, Suppl. 8, 2004, p. S23-S34.
Foran, et al., Botulinum neurotoxin Cl cleaves both syntaxin and SNAP-25 in intact and permeabilized chromaffin cells: correlation with its blockade of catecholamine release, Biochemistry. Feb. 27, 1996; 35(8): 2630-6.
Gerber, et al., Molecular determinants of regulated exocytosis, Diabetes, 2002, 51, Supplement 1:s3-11.
Hafez, et al., Tunable pH-Sensitive Liposomes Composed of Mixtures of Cationic and Anionic Lipids 79 Biophysical Journal 1438-1446 (2000).
Hajduch, et al., Proteolytic cleavage of cellubrevin and vesicle-associated membrane protein (VAMP) by tetanus toxin does not impair insulin-stimulated glucose transport or GLUT4 translocation in rat adipocytes, Biochem. J. Jan. 1, 1997; 321 (Pt 1):233-8.
Halpern, J., "Sequence Homology between Tetanus and Botulinum Toxins Detected by an Antipeptide Antibody", Infection and Immunology, vol. 57, No. 1, Jan. 1989, p. 18-22.

(56) References Cited

OTHER PUBLICATIONS

Harrington, et al., Liposomally Targeted Cytotoxic Drugs For The Treatment Of CancerJournal Of Pharmacy and Pharmacology, 2002, 54: 1573-1600.
Heckmann, M. et al., Amelioration of body odor after intracutaneous axillary injection of botulinum toxin A,Arch Dermatol., Jan. 2003 139(1):57-9).
Kazutetsu, et al., Alveolar Wall Apoptosis Causes Lung Destruction and Emphysematous Changes, American Journal of Respiratory Cell and Molecular Biology, vol. 28, 2003, 555-562.
Keller, et al., Uptake of Botulinum Neurotoxin into Cultured NeuronsBiochemistry 2004, 43, 526-532.
Knutson, et al., Topical Drugs2 Remington: The Science and Practice of Pharmacy 866-885, Alfonso R. Gennaro.
Koriazova, L., et al., "Translocation of Botulinum Neurotoxin Light Chain Protease Through the Heavy ChainChannel," Nature Structural Biology, vol. 10., No. 1, Jan. 2003, p. 13-18.
Kramer et al Journal of Neurology vol. 250 No. 2 pp. 188-193 Feb. 1, 2003.
Labhasetwar, Nanoparticles For Drug Delivery, Pharm. News 4, 28-31, 1997.
Leifert, et al., "Translocatory Proteins" and "Protein Transduction Domains": A Critical Analysis of Their Biological Effects and the Underlying Mechanisms, Molecular Therapy, 2003, 8:13-20.
Lindgren, et al., Translocation Properties Of Novel Cell Penetrating Transportan And Penetratin Analogues: Bioconjug. Chem. 2000, 11:619-626.
Lindsay, Peptide-Mediated Cell Delivery: Application in Protein Target Validation Current Opinion in Pharmacology 2002, 2:587-594.
Maisey, E., et al., "Involvement of the Constituent Chains of Botulinum Neurotoxins A and B in the Blockage ofNeurotransmitter Release," European Journal of Biochemistry, vol. 177, 1988, p. 683-691.
Maksymowych, A., et al., "Pure Botulinum Neurotoxin is Absorbed from the Stomach and Small Intestine and Produces Peripheral Neuromuscular Blockade,"Infection and Immunity, vol. 67., No. 9, Sep. 1999, p. 4708-4712.
Mayer, Membrane Fusion In EukaryOtic Cells, Annu. Rev. Cell Dev. Biol. 2002. 18:289-314.
Morris, et al., A peptide carrier for the delivery of biologically active proteins into mamalian cells, nature Biotechnology, vol. 19, pp. 1173-1176, 2001.
Nairn, Solutions, Emulsions, Suspensions and Extracts2 Remington: The Science and Practice of Pharmacy 1495-1523, Alfonso R. Gennaro ed., 19th ed., 1995.
Nath, et al., Involvement of a botulinum toxin-sensitive 22-kDa G protein in stimulated exocytosis of human neutrophils., J. Immunol. (1994) 152:1370-9.
O'Connor, et al., Powders2 Remington: The Science and Practice of Pharmacy 1598-1614, Alfonso R. Gennaro ed., 19th ed., 1995.

* cited by examiner

CELL MEMBRANE TRANSLOCATION OF REGULATED SNARE INHIBITORS, COMPOSITIONS THEREFOR, AND METHODS FOR TREATMENT OF DISEASE

CROSS REFERENCE TO RELATED APPLICATIONS

This application is a continuation of U.S. application Ser. No. 10/545,872 (pending), filed Aug. 17, 2005, entitled Cell Membrane Translocation of Regulated Snare Inhibitors, Compositions Therefor, and Methods for Treatment of Disease, which is a U.S. national phase entry under 35 U.S.C. §371 of International Application No. PCT/US04/05436 (expired), filed Feb. 24, 2004, entitled Cell Membrane Translocation of Regulated Snare Inhibitors, Compositions Therefor, and Methods for Treatment of Disease, which claims the benefit of U.S. Provisional Application No. 60/449,107 (expired), filed Feb. 24, 2003, entitled Compositions of Amphipathic Pharmaceuticals and Methods For Their Use, by I. Sanders, each of which applications are hereby incorporated herein by reference in their entireties.

FIELD OF THE INVENTION

This invention relates to translocation of bioactive molecules through cell membranes. More specifically, the invention relates to cell membrane translocation of regulated SNARE inhibitors, compositions and formulations thereof, and methods for treatment of disease.

BACKGROUND OF THE INVENTION

A promising area of pharmaceutical intervention is the use of macromolecules that act within cells. These include gene therapy, natural and recombinant toxins, immunotoxins, and antibodies. One significant technical barrier is passing the bioactive macromolecules from the extracellular fluid (the cis-side of the membrane) through the bilipid cell membrane to the cytoplasm (the trans-side).

Generally, macromolecules enter the cell by endocytosis. Endocytosis is an ongoing process whereby the cell recycles its membrane components and internalizes molecules bound to its surface. During endocytosis, the cell membrane invaginates into the cell's interior and then pinches off to form an endosome. Endosomes comprise a complete membrane that encloses its internal contents (the cis-side) and separates them from the cytoplasm of the cell (the trans-side). After endosome formation, proton pumps within its membrane act to reduce the pH within the endosome to approximately 5.0 to 5.5. At a later stage, many endosomes merge with lysosomes where their contents are degraded.

In one mechanism of endocytosis-type cell-membrane transport, the toxins remain in endosomes that undergo processing and ultimately merges with the endoplasmic reticulum of the cell. In the endoplasmic reticulum there is a membrane transporter that translocates the molecule into the cytoplasm. This route is used by cholera toxin and the toxin ricin. This route is difficult for most complex pharmaceuticals as they are degraded during the prolonged endosomal stage.

In a second, and probably the most common, method by which toxins, viruses and pharmaceuticals with amphipathic regions (i.e., regions that contain both hydrophobic and hydrophilic amino acids) enter cells, the toxin is internalized in the endosome as described above and then passes through the endosome membrane when the interior pH becomes acidic. At acidic pH, these amphipathic regions become more hydrophobic and merge with the endosome membrane. Once incorporated in the membrane, a pore is formed through which the toxic or catalytic part of the molecule passes from the endosome into the cytoplasm.

The amphipathic bacterial toxins include the clostridial neurotoxins from *Clostridia botulinum, berati, butyricum* and *tetani, Clostridia botulinum* toxin C2, *Clostridia perfringens* iota toxin, *Clostridia difficile* B toxin, anthrax toxin, diptheria toxin, and others. All of these toxins have a basic two-component protein structure: (1) a toxic protein chain containing a catalytic domain that can perform intracellular intoxication; and (2) a protein with both a binding and translocation domain. In most toxins, the two protein components are linked covalently or tightly coupled by non-covalent forces. In others, such as Botulinum toxin C2, the two components are independent proteins, and they only interact on cell surfaces. Anthrax toxin is unusual in that the same binding/translocation protein chain, called protective antigen, can translocate either of two independent toxic proteins, lethal factor and edema factor. The binding/translocation protein chain is further subdivided into: (1) a binding domain, which recognizes one or more receptors on the surface of cells; and (2) an amphipathic domain, which can translocate the molecule through cellular or endosome membranes at acidic pH.

The binding/translocation protein chains from these wild type toxins have been separated and used as carriers to bring molecular 'cargo' into cells: other biological useful molecules (e.g., tetanus neurotoxin/superoxide dismutase WO/0028041A1: Delivery Of Superoxide Dismutase To Neuronal Cells, hereby incorporated herein by reference). Toxins used in this manner include botulinum and tetanus toxins, diptheria toxin, botulinum toxin C2, and anthrax toxin. The amphipathic regions have been sequenced for the translocation domains of many bacterial toxins and viruses, and based on this knowledge, novel recombinant amphipathic moieties have been produced. At present some of these natural and recombinant amphipathic proteins have been shown to capable of translocating across the endosome membrane when the endosome interior becomes acidic. However, few amphipathic protein conjugates are presently approved for clinical use.

1. Botulinum Neurotoxin

Wild type clostridial neurotoxins, specifically those from *Clostridia botulinum*, are amphipathic protein conjugates with unique properties that make them beneficial in medical applications. First, in their natural or wild type form, they have specificity for neurons, particularly motor neurons. Second, they can block neuromuscular transmission for extended periods, from days to months depending on the serotype. Third, in most clinical applications they have been used at doses that are below the level of immunological recognition. Fourth, as they are remarkably safe for human use when injected into local areas such as muscles because there is little systemic spread of the toxin.

The clostridial neurotoxins include seven serotypes of botulinum neurotoxins, termed A-G (A, B, C1, D, E, F, and G), and a single serotype of tetanus toxin (tetanus neurotoxin). These toxins all have a molecule size of ~150 kD and are comprised of a heavy-chain (~100 kD) and a light chain (~50 kD) that are covalently linked by a disulphide bridge at their N-terminals. The heavy chain consists of the binding domain (fragment C) at the C terminal and a translocation domain (fragment B, which is the amphipathic protein) at the N-terminal end. The light chain (fragment A) is the toxic domain, however, it also contains its own small amphipathic region. These neurotoxins are exceptional due to their specific binding to neurons and their specific catalytic action on the SNARE proteins, which are involved in neurotransmission. Botulinum neurotoxins A, C, and E cleave SNAP-25, in addition botulinum neurotoxin/C cleaves syntaxin 1. botulinum neurotoxins B, D, F, G and tetanus toxin cleave VAMP-2.

The C fragments of the clostridial neurotoxins have affinity for the presynaptic membrane of neurons, and particularly the membrane of motor neurons. Clostridial neurotoxin binding is believed to involve two receptors: (1) polysialo-gangliosides accumulate clostridial neurotoxins on the plasma membrane surface, and (2) protein receptors then mediate specific endocytosis. This hypothesis was supported by the demonstration of the binding of botulinum neurotoxins B to the neuronal membrane protein synaptotagmin in the presence of GT1b, and the recent identification of GPI-anchored glycoproteins in neuronal rafts as specific receptors for the HC-fragment of tetanus neurotoxin.

After a clostridial neurotoxin binds to the presynaptic surface, it is internalized by incorporation into endosomes. When the interior of the endosome reaches about pH 5.5, the amphipathic B-fragment merges with the membrane and forms a pore that allows the light chain to pass through to the cell's cytoplasm. While passing through the membrane the disulfide bond is broken and the light chain is released into the cytoplasm and exerts its toxic effect.

The toxic action of all clostridial neurotoxin light chains is to cleave proteins necessary for attachment of internal vesicles to the cell membrane. The production and docking of these vesicles is a highly regulated process that is present in all eukaryotic cells including single-cell organisms such as yeast. The vesicle membranes merge with the cell membrane thereby adding new membrane bound proteins while simultaneously discharging the vesicle's contents into the extracellular environment. In neurons, these vesicles contain neurotransmitters and neuropeptides. Botulinum neurotoxin A and E cleaves SNAP-25; botulinum neurotoxin C cleaves SNAP-25 and syntaxin 1; and tetanus neurotoxin and botulinum neurotoxin types B, D, F and G cleave VAMP (vesicle associated membrane protein, also called synaptobrevin).

Botulinum neurotoxins A and B are the serotypes currently approved by the FDA for human use. Direct injection into extra-ocular muscles was found to be beneficial in the treatment of strabismus. Subsequently, botulinum neurotoxin A has been used to treat a variety of spastic or hyper-functional muscle disorders. Botulinum neurotoxin A has also been used for the treatment of smooth muscle hyper-function (e.g., cricopharyngeal spasm). Recently, botulinum neurotoxin has been used for treatment in connection with the cholinergic nerves of the autonomic nervous system. These uses include arresting of secretions, such as sweating and post-nasal drip.

2. Tetanus Neurotoxin

Tetanus neurotoxin exhibits fundamental differences relative to botulinum neurotoxin. First, tetanus neurotoxin binds and enters into all peripheral neurons: motor, autonomic (parasympathetic and sympathetic) and sensory neurons, including those that transmit pain signals. In contrast, botulinum neurotoxin binds and enters only motor neurons and autonomic parasympathetic neurons.

Second, at physiological doses, in contrast to botulinum neurotoxin, tetanus neurotoxin does not use the acidified endosomal pathway to enter peripheral neurons. Although internalized in the same manner as botulinum neurotoxin, the specific receptors to which tetanus neurotoxin binds allows for preferential sorting of the endosome. Tetanus-neurotoxin-containing endosomes become non-acidified vesicles that are transported retrograde to the motor neuron cell body in the central nervous system or sensory ganglia. Upon reaching the cell body, tetanus neurotoxin is released into the presynaptic space and preferentially binds to inhibitory neurons that use glycine or GABA as their neurotransmitter. When tetanus neurotoxin is taken up by inhibitory neurons in the central nervous system, it then goes through the acidified endosomal stage and acts much like that of botulinum neurotoxin in peripheral neurons. Accordingly, tetanus neurotoxin preferentially blocks inhibitory activity. The resulting unopposed excitatory activity causes muscles to contract uncontrollably, a condition called spastic paralysis. Although the clinical condition known as tetanus is a systemic intoxication, it is known that tetanus neurotoxin can also act in localized areas in mammals. At doses comparable to those that cause paralysis with botulinum neurotoxin A, tetanus neurotoxin causes a local increase in motor, autonomic and/or sensory neuron activity.

At high doses tetanus neurotoxin can cause paralysis by blocking neurotransmission both centrally and peripherally. At doses, 10 to 2000 times that needed for excitation, tetanus neurotoxin blocks both excitatory and inhibitory neurons in the central nervous system. These high doses risk local and systemic side effects. In addition, the binding domain of tetanus neurotoxin can be separated from the remainder of the molecule by digestion with the enzyme papain. Upon digestion, the resulting fragment is called tetanus neurotoxin A-B fragment and contains the light chain connected by a disulphide bridge to the translocating domain of the heavy chain. Since the A-B fragment is missing its binding fragment, it can no longer both bind and undergo retrograde transport. But the A-B fragment can cross the cell membrane and paralyze the neuromuscular synapse and cause a flaccid paralysis. But this effect requires tens of thousands more molecules of A-B fragment to than that needed for the excitation caused by wild type tetanus neurotoxin. The mechanism for this effect seems to the non-specific pinocytosis of tetanus neurotoxin A-B fragment by cells.

Finally, another unusual attribute of tetanus neurotoxin that it is internalized by some non-neuronal cell types. The most clinically useful of these are the macrophages that migrate to areas of inflammation. Tetanus neurotoxin blocks the release of inflammatory mediators and enzymes by macrophages, thereby decreasing the inflammatory response.

International Application WO 02/00172 (published Jan. 3, 2002), hereby incorporated herein by reference, teaches a wide variety of methods for using tetanus neurotoxin by increasing or decreasing neural activity or non-neural cellular activity.

The wild type amphipathic protein conjugates such as clostridial neurotoxin conjugates have wide potential as therapeutic agents. For example, the selective motor neuron binding of the neurotoxin heavy chain has been combined with the enzyme superoxide dismutase for the treatment of motor neuron degenerative diseases. The CNS transport abilities of the tetanus neurotoxin heavy chain or its He fragment are especially useful as it is one of the few vectors that can bypass the blood brain barrier (rabies and herpes virus being two others). Due to the universal nature of the vesicle docking process in cells, the use of clostridial neurotoxin light chains combined with cell-type specific amphipathic proteins holds great promise for the treatment of a wide variety of clinical conditions. Very specific targeting of cell types is plausible using recombinant technology to incorporate monoclonal immunoglobulins into amphipathic proteins. Unfortunately, however, as discussed below, introduction of these novel compounds is limited because of the inefficiencies of the endosomic process.

3. Disadvantages of Endosomic Transport of Amphipathic Protein Conjugate into Cells Although, as discussed above, amphipathic protein conjugates—such as clostridial neurotoxins—have potential medical applications, their usefulness is limited by inefficient transport into cells. As discussed above, amphipathic protein conjugates enter cells by way of endocytosis and then require translocation across the endosome membrane. This is a disadvantage for a variety of reasons. In most cases, only a small percentage of the active moieties survive the various steps of cell binding, endocytosis, endosome acidification, and translocation. This inefficiency increases the incidence of side effects and the induction of immune reactions.

Binding of some amphipathic protein conjugates to cell membranes is highly specific to the cell type. This is an advantage for some conditions but precludes their use in other conditions where binding affinity is low. Further, the binding of the amphipathic protein conjugates to the surface of membranes prior to endocytosis can be prolonged as they await the normal cell turnover of cell membrane to reach them. Therefore, these molecules are exposed to degrading extracellular enzymes, and in some cases neutralizing antibodies. Once internalized into the cell within an endosome, acidification of the endosome to induce release of the active moiety into the cell can take hours. Accordingly, translocation across the endosome membrane is the rate-limiting step in the entry of the active moiety into the cell. Another disadvantage of amphipathic protein conjugates, is that the endosome contains its own assortment of enzymes that can degrade the conjugate. For example, during the treatment of cancer, the development of multi-drug resistance by cancer cells is believed to involve molecular changes in the endosome that cause the drug to be removed from the cell.

Therefore there is a need in the art for a method allowing amphipathic protein conjugates to bypass the endosomal stage and translocate directly across cell membranes into cytoplasm.

Basic research studies have demonstrated direct membrane translocation by way of culture mediums that mimic the acidic conditions of the endosome. In 1980, it was found that when cells in culture were exposed to diphtheria toxin in an acidic medium, the toxin would translocate directly into the cytoplasm. This advance was of basic science importance as it simplified the study of how the toxin interacts with cell membranes,. This is a much easier task then studying the toxin's interaction with the membranes of an internal organelle such as the endosome. Subsequently the ability to translocate directly into the cytoplasm has been demonstrated for a number of bacterial toxins such as anthrax toxin (lethal factor and adenylate cyclase), Clostridium botulinum C2 toxin, Clostridium difficile toxin B, *Clostridia sordellii* lethal toxin and the clostridial neurotoxins.

The advantages of direct translocation on the efficiency of an amphipathic protein-conjugates has been demonstrated for the *Clostridium sordellii* lethal toxin. When cultured cells were exposed to lethal toxin at pHs from 4.0 to 5.0 for only 10 minutes it increased the rate of intoxication over 5-fold, lowered the minimal intoxicating dose by over 100-fold, and allowed complete substrate modification within 2 h, instead of the 11 hours needed for the endosomal route.

Regarding clostridial neurotoxin, native and recombinant botulinum neurotoxin attaches to artificial bilipid layers coated with gangliosides, and translocate their light chains within seconds after exposure to pH 5 on the cis side when the trans side is held at pH 7.0. In addition, acidic cell culture medium allows clostridial neurotoxin to enter cells that have no specific binding sites. For example, botulinum neurotoxin-B has been demonstrated to translocate into cultured colon carcinoma cells and neutrophils by incubation in medium at pH 4.7. Moreover, even isolated clostridial neurotoxin light chains can translocate rapidly through bilipid membranes at pH 4.0. This effect is believed to be due to the presence of a separate amphipathic region in the light chain.

In summary, acidic medium rapidly speeds the translocation of amphipathic proteins-conjugates into cells they normally enter by the endosomal route, allows them to enter cells that they normally cannot enter, and in certain cases even allows the direct entry of the "cargo" molecule into cells.

Note that all the above-described experiments were performed to study how membrane translocation occurs or to study the intracellular effects of specific molecules and do not teach, suggest or even anticipate the use of acid mediated translocation in vivo.

In addition to amphipathic proteins, there are others possible mechanisms of protein translocation into cells. Membrane transduction proteins have recently been identified that directly bind and possibly merge with membranes and can translocate molecular cargo into cytoplasm. These proteins include part of the human immunodeficiency virus Tat, Drosophilae Antennapedia (Penetran), and Transportan (13 amino acids from galanin and wasp venom mastoporan). Based on studies of these proteins artificial membrane transduction proteins have been developed such as oligoarginine. Finally there are a variety of newer methods being studied that involve encapsulating the bioactive cargo molecule. The use of these substances in conjunction with a toxic moiety could substitute for the amphipathic moiety in all examples disclosed in this specification.

The present invention may be understood more fully by reference to the following detailed description and illustrative examples, which are intended to exemplify non-limiting embodiments of the invention.

SUMMARY OF THE INVENTION

The invention relates to methods and compositions for improved delivery of bioactive substances into cells within a localized part of the body by way of translocation agents. The invention encompasses methods of delivering the substance to the body part, methods to facilitate the binding to and/or translocating of the bioactive substance across cell membranes, and methods of protecting the bioactive substance from neutralizing antibodies.

The invention also relates to compositions and methods of modulating cellular function and treatment of disease in mammals comprising locally administering a bioactive substance—preferably, a regulated SNARE inhibitor—and a translocating agent to the mammal. Regulated SNARE inhibitors include bacterial neurotoxins, such as clostridial neurotoxins; tetanus neurotoxin; the free light chain portions of bacterial neurotoxins and tetanus neurotoxin; and IgA protease. Translocating agents include acids, acidic environments, encapsulating vectors, and protein transduction domains.

In one embodiment, the bioactive substance is delivered relatively non-specifically to mammalian cells (preferably neurons) in a localized area of the mammal, thereby avoiding many difficulties with systemic administration.

In another embodiment, the invention relates to facilitating the binding of bioactive substances to mammalian cell membranes, whereupon, the bioactive substance is incorporated by way of the cell's natural internalization mechanisms.

In another embodiment, the invention relates to bypassing the natural cell internalization mechanisms and translocating the bioactive substances directly across the cell membrane.

In still another embodiment, the invention relates to methods for combining the bioactive substances with translocating agents or other moieties that facilitate cell membrane binding and/or entry of bioactive substances into cells.

The bioactive substance for use in the invention can be any substance or molecule that induces a biological response in mammalian cells or a therapeutic effect in a mammal. Preferably, the bioactive substance is a bioactive part of a natural toxin. More preferably, the bioactive substance is a regulated SNARE inhibitor, most preferably, the bioactive substance is the light chain of a clostridial neurotoxin, preferably, the free light chain or its analogue, a protein called IgA protease.

DETAILED DESCRIPTION OF THE INVENTION

1. Definitions 1.1 Regulated SNARE Inhibitors

As used herein, the term "regulated SNARE inhibitor" means any molecule that inhibits the function of or cleaves one or more of the SNARE proteins involved in regulated exocytosis (regulated SNAREs). Regulated exocytosis requires regulated membrane fusion, principally between an internal vesicle (such as an endosome) and the cell membrane. The minimal SNARE protein machinery involved in regulated exocytosis (regulated SNARE) are: (1) vSNARE, VAMP-2; and (2) the tSNAREs, SNAP-25 and syntaxin-1, and the isoforms and splice variants of these proteins as defined below.

Preferably, "regulated SNARE inhibitors" consist of light chains of clostridial neurotoxins. These include the entire light chain or active fragment thereof from the botulinum neurotoxin serotypes A, B, C1, D, E, F and G and tetanus neurotoxin.

The amino acid sequences of the clostridial neurotoxin light chains are known, and these sequences can be modified by addition, deletion, or substitution of amino acids, or otherwise chemically altered, whereby the protein is modified but the inhibitory effect on at least one regulated SNARE is retained. These modifications are accomplished by methods well known in the art. "Regulated SNARE inhibitors" as used herein, includes all such modified clostridial neurotoxin light chains.

The amino acid sequence of regulated SNARE inhibitors can be rearranged using recombinant techniques yielding molecules that retain regulated SNARE inhibitory activity. The term "regulated SNARE inhibitor" as used herein includes all such recombinantly rearranged molecules.

The term "regulated SNARE inhibitor" also includes all natural analogues of clostridial neurotoxin light chains, such as those produced by the bacteria Neisseria gonorrhea, which produces the regulated SNARE inhibitor IgA protease. IgA protease can cleave the IgA class of antibody as well as VAMP-2.

The term "regulated SNARE inhibitor", as used herein, further includes: (1) proteins and other molecules that can cleave or inhibit regulated SNAREs including non-functional fragments of regulated SNARE proteins (Apland J P et al.; *Inhibition of neurotransmitter release by peptides that mimic the N-terminal domain of SNAP*-25, J. Protein Chem. (2003) 22:147-53), hereby incorporated herein by reference. (2) antibodies that bind to regulated SNAREs Breedveld F C: *Therapeutic monoclonal antibodies* Lancet 2000; 355: 735-40), hereby incorporated herein by reference; and (3) antibodies and other molecules that interact with additional cell proteins in the fusion process. It is known that altered and non-functional forms of the regulated SNAREs can interfere with regulated exocytosis. In addition, antibodies can bind to the regulated SNAREs and inhibit their function.

Furthermore, in vivo, the regulated SNAREs interact with a many other proteins that are involved in the fusion process, and these too can be targeted for inhibition. Proper vesicle trafficking involves vesicle formation, maturation, transport, docking, priming, fusing, and recycling. A non-limiting list of associated proteins involved in regulated vesicle trafficking and exocytosis includes: Synaptogamin, Synaptophysins, Peptide amidase, Synapsins, Synaptogyrins, Cytochrome b561, GABA/glutamate transporters, Rab3A, B, and C, Processing peptidases, Synaptotagmins 1 & 2 (PC1, PC2, CPE etc), SV2s, IA-2/phogrin, SVOP, SCAMPs, Synaptobrevins, Vacuolar proton pump, Cysteine string protein, Zinc transporters, Catecholamine transporters, Chloride transporter, SM proteins particularly Munc-13 and 18, and hrs. The participation of these proteins is described in various review articles (Gerber S H, Sudhof T C: *Molecular determinants of regulated exocytosis*, Diabetes, 2002, 51, supplement 1:s3-11, hereby incorporated herein by reference; Mayer A: *Membrane fusion in eukaryotic cells,* Annu. Rev. Cell Dev. Biol. 2002. 18:289-314), hereby incorporated herein by reference.

Preferably, a regulated SNARE inhibitor is a protein, protein fragment, or conjugate thereof. Preferably, regulated SNARE inhibitors can cross from the extracellular fluid through the cell membrane and into the cell cytoplasm. Examples of regulated SNARE inhibitors include, but are not limited to, amphipathic bacterial toxins, such as clostridial neurotoxins from *Clostridia botulinum, berati, butyricum* and *tetani*. More preferably, the regulated SNARE inhibitor is the light chain portion of clostridial neurotoxins. In another preferred embodiment, the regulated SNARE inhibitor is IgA protease.

1.2 Regulated SNARES

As used herein, regulated SNARE proteins are proteins involved in regulated vesicle trafficking and exocytosis. Regulated exocytosis requires regulated membrane fusion, principally between an internal vesicle and the cell membrane. The minimal SNARE protein machinery involved in regulated exocytosis are: (1) vesicle SNAREs VAMP-2; and (2) target SNARES: SNAP-25 and syntaxin-1. Also included under the meaning of regulated SNAREs are isoforms and splice variants of these proteins, and putative regulated SNARES as recognized by their selective inhibition by one or more clostridial neurotoxins:

1.2.1 VAMP

VAMP-2, also called synaptobrevin, has two isoforms numbered 1 and 2 (Rossetto O. et al., VAMP/Synaptobrevin isoforms 1 and 2 are widely and differentially expressed in non-neuronal tissues, J. Cell. Biol. (1996) 132:167-79), hereby incorporated herein by reference. Also used herein and included under the definition of regulated SNAREs is cellubrevin, which is an isoform of VAMP cleaved by tetanus neurotoxin (Hajduch E et al., *Proteolytic cleavage of cellubrevin and vesicle-associated membrane protein (VAMP) by tetanus toxin does not impair insulin-stimulated glucose transport or GLUT4 translocation in rat adipocytes*, Biochem. J. 1997 Jan. 1; 321 (Pt 1):233-8), hereby incorporated herein by reference, and botulinum toxin B (Tamori Y et al., *Cleavage of vesicle-associated membrane protein (VAMP)-2 and cellubrevin on GLUT4-containing vesicles inhibits the translocation of GLUT4 in 3T3-L1 adipocytes* Biochem. Biophys. Res. Commun. 1996 Mar. 27; 220(3): 740-5), hereby incorporated herein by reference, and botulinum D (Cheatham B et al., *Insulin-stimulated translocation of GLUT4 glucose transporters requires SNARE-complex proteins* Proc. Natl. Acad. Sci. USA. 1996 Dec. 24; 93(26): 15169-73), hereby incorporated herein by reference.

1.2.2 SNAP

SNAP 25 has 2 splice variants termed SNAP 25 A and B and these are included under the definition, as they participate in regulated exocytosis and are cleaved by CNT. Another example of an regulated SNARE is the putative SNAP variant G22K, that is involved in regulated exocytosis of neutrophil white blood cell granules and is cleaved by botulinum toxin D. (Nath J. et al., Involvement of a botulinum toxin-sensitive 22-kDa G protein in stimulated exocytosis of human neutrophils., J. Immunol. (1994) 152: 1370-9), hereby incorporated herein by reference.

1.2.3 Syntaxin

Syntaxin 1 has two isoforms, syntaxin 1A and 1B, and both are cleaved only by botulinum toxin C1 (Foran P et al.: Botulinum neurotoxin C1 cleaves both syntaxin and SNAP-25 in intact and permeabilized chromaffin cells: correlation with its blockade of catecholamine release. Biochemistry. 1996 Feb. 27; 35(8): 2630-6), hereby incorporated by reference herein.

1.3 Free Light Chains of Bacterial Neurotoxins

As used herein, the term "free light chains" refers to the light chains of bacterial neurotoxins or a biologically active fragment thereof without the heavy chain binding or translocation domains. Notably, Clostridial neurotoxins light chains contain a small translocation domain at their N-terminal that is separate from that present on heavy chains. IgA protease is also believed to have any translocation domain. Non-limiting examples of free light chains include the light chains derived from clostridial neurotoxins, such as botulinum neurotoxin serotypes (including botulinum neurotoxin serotype is A, B, C1, D, E, F and G), tetanus neurotoxin. Another non-limiting example is the free light chain is IgA protease.

1.4 Translocation or Translocating

As used herein, the terms "translocation" or "translocating" with respect to translocation of regulated SNARE inhibitors across cell membranes means transfer of a molecule across the cell membrane. This transfer may or may not be accomplished by the formation of endosomes. "Direct translocation" means that the molecule passes through the cell membrane without being internalized into endosomes.

1.5 Translocating Agent

As used herein, the phrase "translocating agent" means any substance, molecule, or environmental condition that facilitates translocation of a bioactive molecule (preferably, a regulated SNARE inhibitor) across a lipid membrane, preferably the outer cell membrane of a mammalian cell. Preferred translocating agents include, but are not limited to, acids or an acidic environment; amphipathic moieties (i.e., molecules or polypeptides that become hydrophobic at pHs other than 7.4, preferably at more acidic pH); protein transduction domains, such as cationic polymers or polypeptides that bind to cell membranes; and encapsulation vectors, which encapsulate the bioactive substance within artificial vesicles that in turn bind or translocate the bioactive substance within mammalian cells. Examples of encapsulating vectors include, but are not limited to, liposomes, niosomes, transferosomes, viruses and nanoparticles.

1.6 Facilitating Translocation

As used herein, "facilitating translocation" means an increase in the number of bioactive moieties (preferably, regulated SNARE inhibitors, more preferably, the free light chains of bacterial neurotoxins) that cross a cellular membrane in a specified time period with the assistance of a translocating agent relative to the number of bioactive moieties that cross the cellular membrane for that time period in the absence of the translocating agent. "Facilitating translocation" also means a decrease in time required for a specified number of bioactive moieties to cross the membrane with the assistance of a translocating agent relative to the time that the specified number of bioactive moieties cross the cellular membrane in the absence of the translocating agent.

Whether translocation has been facilitated can be determined by assays well known in the art, for example, by measuring one or more of cell survival (Williamson L and Neale E: *Syntaxin and 25-kDa synaptosomal-associated protein: Differential effects of botulinum neurotoxins C1 and A on neuronal survival;* J Neurosci Res 52:569-583 (1998), hereby incorporated herein by reference; cell division (Conner S & Wessel G M: Syntaxin Is Required for Cell Division Molecular Biology of the Cell, Vol. 10, 2735-2743, August 1999), hereby incorporated herein by reference; by membrane replacement (Cheatham B et al., Insulin-stimulated translocation of GLUT4 glucose transporters requires SNARE-complex proteins., Proc. Natl. Acad. Sci USA, 1996, 93:15169-73), hereby incorporated herein by reference; or by exocytosis (Keller J. et al., Uptake of Botulinum Neurotoxin into Cultured Neurons, Biochemistry 2004, 43, 526-532), hereby incorporated herein by reference.

1.7 Cell Membrane Binding

As used herein, the term "binding" with respect to binding of molecules to cell membranes means that the molecule bonds non-covalently to the membrane or the exposed proteins, lipid or carbohydrate moieties of membrane embedded molecules.

1.8 Cell Membrane Fusion

As used herein, "fusion" means that the merging of lipid membranes or that hydrophilic moieties of a molecule have become embedded into the membrane.

1.9 Amphipathic Moieties or Proteins

As used herein, the terms "amphipathic moieties" or "amphipathic proteins" means natural (wild type) or artificially produced moieties or proteins that are capable of changing from hydrophilic to hydrophobic secondary to changes in pH, either increased acidity or increased alkalinity. Preferably in the hydrophobic state at least part of the molecule can fuse with lipid membranes.

1.10 Amphipathic Protein Conjugates

As used herein, the term "amphipathic protein conjugate" means a molecule or molecule complex comprising an amphipathic moiety or amphipathic protein (as defined above) that is associated with a bioactive substance and that is capable of translocating the bioactive substance into the cytoplasm of a cell, preferably, at acidic pH.

1.11 Local Delivery or Local Administration

As used herein, the terms "local delivery" or "local administration", with respect to delivery of a regulate SNARE inhibitor to a mammal, means delivery or administration of the regulated SNARE inhibitor to a local part of the body, through or into the skin or mucosa of a mammal. Preferably, local delivery is effected without significant absorption of the regulated SNARE inhibitor into the mammal's blood stream with subsequent systemic distribution. The purpose of local delivery is to elicit a local affect in the area (selected site) of administration. Preferably, local delivery or administration is by way of a pharmaceutically effective formulation.

1.12 Therapeutically Effective Amount

The term "therapeutically effective amount" with respect to a regulated SNARE inhibitor means an amount of the regulated SNARE inhibitor, preferably, a non-toxic amount, sufficient to treat, prevent, or reduce the occurrence or magnitude of symptoms of a disease or medical condition being targeted. Preferably, when administered to a mammal, a therapeutically effective amount is administered in a pharmaceutically effective formulation.

1.13 Modulating Cellular Function

As used herein the phrase "modulating cellular function" means any change in a cell's function, preferably, a change due to a change in the rate of the number of membrane fusions occurring in the cell, more preferably, a decrease in said fusion events, and most preferably a decrease in regulated membrane fusion occurring as part of regulated exocytosis.

1.14 Modulatorily Effective Amount

The term "modulatorily effective amount" with respect to a regulated SNARE inhibitor means an amount of the regulated SNARE inhibitor, preferably a non-toxic amount sufficient to modulate cellular function when locally administered to a mammal. Preferably, when administered to a mammal, a modulatorily effective amount is administered in a pharmaceutically effective formulation.

1.15 Wild Type

As used herein, the term "wild type" or "natural toxins" means naturally found proteins and toxins from plants, animals, or microbes. Numerous modifications and alterations can be made to the wild type molecule. At present, recombinant techniques allow for the formation of a clostridial neurotoxin molecule in which any part of the molecule can be replaced, either by an analogous part of another clostridial neurotoxin, or by a completely different molecule. In addition the protein can be chemically modified in various ways to decrease immunogenicity, decrease diffusion from the site of application, increase binding, biological persistence, toxicity or for other reasons. For example, the light chain of botulinum neurotoxin/A has amino acid fragments for various secondary modification sites (hereinafter "modification sites") including, but not limited to, N-glycosylation, casein kinase II (CK-2) phosphorylation, N-terminal myristylation, protein kinase C (PKC) phosphorylation and tyrosine phosphorylation (U.S. 2002/0127247A1: Modified clostridial neurotoxins with altered biological persistence), hereby incorporated herein by reference. Nucleic acid itself can be used in place of protein and inserted into cells for later translation into protein. (WO 14570 Recombinant Activatable Neurotoxins), hereby incorporated herein by reference. Regulated SNARE inhibitors include all these changes and modifications.

1.16 Chimeric or Hybrid Toxin

As used herein, the term "chimeric" or "hybrid toxin" refers to bioactive molecules either created by joining parts derived from two or more natural toxins (U.S. Pat. No. 6,444,209: Hybrid botulinal neurotoxins, hereby incorporated herein by reference) or created by joining all or part of a natural toxin with all or part of another large molecule, such as an antibody. In the wild, it has been found that some strains of Clostridia produce a hybrid toxin composed of proteins chains from two different serotypes. But with recombinant genetics this can be accomplished artificially. Therefore, the light chain of any CNT can be combined with the heavy chain of any other. For example, a chimeric toxin consisting of the "heavy" (ca. 100,000 MW) chain of botulinum toxin and the "light" (ca. 50,000 MW) chain of tetanus toxin was constructed and found to have six times the potency of native tetanus toxin (Weller, U. et al., "*Cooperative Action of the Light Chain of Tetanus Toxin and the Heavy Chain of Botulinum Toxin Type A on the Transmitter Release of Mammalian Motor Endplates*" Neurosci. Letters (1991) 122: 132-134), hereby incorporated herein by reference.

1.17 Local Tissue Acidification

As used herein, the term "Acidification" means creation of acidic conditions in mammalian tissue in relation to the neutral pH 7.4 of extracellular fluid. "Acid" or "acidic solution" means a pharmaceutically safe solution or other carrier that can be used to decrease the pH, preferably to facilitate translocation of amphipathic moieties or proteins. "Buffered acid solutions" as used herein mean the inclusion of a buffer that serves to maintain the solution at a desired pH, preferably, the pH that is most preferable for translocation of the regulated SNARE inhibitor.

1.18 "Units of Toxin"

As used herein, the phrase "units of toxin" means the amount that causes death in 50% of 20 gram Swiss Webster mice upon injection. As used herein when "units" refer to an entity that cannot cause animal death by themselves, such as compositions of clostridial neurotoxin light chains, it refers to the molar equivalent of light chains that is obtained from the dose of whole toxin that can be assayed. As an illustrative example if a unit of a particular botulinum toxin serotype weighs 6 nanograms, than a unit of botulinum toxin of light chain composition weighs 2 nanograms. A "unit" of IgA protease is fifty times more by weight than a unit of tetanus neurotoxin light chains as defined by a biological assay of regulated SNARE inhibition of nor-epinephrine by chromaffin cells (Binscheck T et al., *IgA protease from Neisseria gonorrhoeae inhibits exocytosis in bovine chromaffin cells like tetanus toxin*, J. Biol. Chem. 1995 Jan. 27; 270(4):1770-4), hereby incorporated herein by reference.

2. Sources or Regulated SNARE Inhibitors

Regulated SNARE inhibitors are readily commercially available, for example, botulinum toxin serotypes A, B, C1, D, E, F, G, tetanus toxin and their light chains are available from List Biological Laboratories (www.listlabs.com) and/or Wako Labs (Japan) and Metabiologics, Inc., Madison Wis.

Botox™ (botulinum type A) is available from Allergan Corporation, Irvine Calif.; Myobloc™ (botulinum toxin type B) is available from Elan, Dublin, Ireland; Dysport™ (botulinum toxin A) is available from Ipsen Speywood, Bath, United Kingdom; IgA protease is available from Cliniqua Corporation, Fallbrook, Calif.

3. Methods of the Invention for Translocating and/or Binding Regulated SNARE Inhibitors In one embodiment, the invention provides methods for binding regulated SNARE inhibitors to the cell membrane and/or translocating regulated SNARE inhibitors across the cell membrane. In one embodiment, the methods of the invention are directed to acid mediated translocation. In another embodiment, the methods of the invention are directed to translocation and binding of regulated SNARE inhibitors by way of protein transduction domains. In yet another embodiment, the methods of the invention are directed to translocation and binding of regulated SNARE inhibitors by way of encapsulation vectors.

In still another embodiment, the methods of the invention are directed to specific binding to or translocating, i.e., the methods of the invention are such that the regulated SNARE inhibitors target specific sub-populations of cells in a local tissue. In another embodiment, the methods of the invention are directed to non-specific binding or translocating, i.e., the methods are such that the regulated SNARE inhibitors bind to or are translocated into all cells in a local tissue.

In another embodiment, the methods of the invention are directed to translocating or binding the light chains of regulated SNARE inhibitors into cells non-specifically. This is therapeutically beneficial as the light chains are specific inhibitors of regulated exocytosis. As the light chains cleave one of the three regulated SNARE proteins this difference among them can be used to therapeutic advantage. More specificity can be achieved by controlling the volume of tissue to which the light chains are delivered.

In one embodiment of the invention, regulated SNARE inhibitors are injected from about one-second to about one hour prior to acidification, thereby allowing regulated SNARE inhibitors to bind prior to translocation. In another embodiment, injection of regulated SNARE inhibitors is performed in conjunction with injection of an acid formulation, thereby causing more general and non-specific binding. The injection of acid solution could also precede injection of the protein of the inventions.

3.1 Acid Mediated Translocation of Regulated SNARE Inhibitors

In one embodiment, the invention provides methods for facilitating the binding and/or direct translocation of regulated SNARE inhibitors upon local delivery of regulated SNARE inhibitors to mammalian tissue having an acidic extracellular environment. Depending on the identity of or the delivery composition of the regulated SNARE inhibitor, its binding and translocation can be facilitated at different pH values.

3.1.1 Generation of an Acidic Extracellular Environment 3.1.1.1 Use of an Acidic Carrier Solution to Generate an Acidic Extracellular Environment In one embodiment of the invention, regulated SNARE inhibitors are administered with an acidic medium, either simultaneously (for example, mixed in an acidic formulation) or consecutively, to effect translocation of regulated SNARE inhibitors into the cell cytoplasm in the local area of injection. This works efficiently with neuronal cells as they contain binding sites but is also effective with non-neuronal cells.

For use in the methods of the invention, preferred pH values of the site of local administration range from about 3.5 to about 7, preferably from about 3.5 to about 4.5 for isolated or free neurotoxin light chains, and, preferably, from about 4.5 to about 6, more preferably, about 5 to about 5.5 for wild type whole CNT.

Acidification in local tissue regions can be the result of local cellular metabolism, the application of acids or acidic solutions, or the formation of hydrogen ions by electrical energy. Examples of acidic solutions suitable for use in the invention include, but are not limited to, phosphoric, acetic, hydrochloric, lactic or hyaluronic acids. These can be in aqueous solution, gels, biodegradable and non-degradable materials. Further examples of pharmacologically suitable acids and buffers are well known in the art and can be found in Goodman and Gillman's The Pharmacologic Basis for Therapeutics, $10^{th}$ edition, McGraw Hill, 2001, hereby incorporated herein by reference.

3.1.1.2 Buffered Compositions of Acidic Solutions

Physiological solutions contain significant amounts of buffer, substances that oppose shifts in pH. Buffers work by absorbing or donating protons to oppose shifts in an acidic or alkaline direction, respectively. The ability of a buffer to oppose a shift in pH depends on its pK and its concentration. The pK corresponds to pH at which equal amounts of the protonated and non-protonated versions of the buffer are present. The concentration of a buffer is preferably described as the amount of protons it can buffer, expressed as milli-equivalents per liter of solution. At the pK the buffer has equal capacity to oppose either an acidic or alkaline shift in pH. However, at the pK only half of the total capacity of a buffer is available to oppose a pH shift. If a buffer has a low pK (acid) and the pH of the solution is high (alkaline) most of the buffer is unprotonated and it has little capacity to resist further shifts toward alkalinity. However, in this example most of the capacity of the buffer is available to oppose pH shifts in the acidic direction, which is usually preferable in body tissues.

In one embodiment of the invention, the acid solution is buffered with a pK at the most appropriate pH that facilitates the translocation of the regulated SNARE inhibitor. primary buffer in extracellular fluids is 3.1.1.3 Electrical Stimulation to Generate an Acidic Extracellular Environment It is one embodiment of this invention that electricity be used to aid in transferring AP-cargo regulated SNARE inhibitor across membranes, preferably to directly translocate the regulated SNARE inhibitor from the extracellular fluid into a cell. into lipids, and across lipid membranes.

Electrical stimulation current within body fluid causes a charge gradient between the anode and cathode electrodes that attracts charged molecules. At relatively high currents electrochemical reactions occur at both the anodal and cathodal electrode surfaces. At the anodal electrode H+ ions are formed, lowering the pH. At the cathodal electrode OH— ions are simultaneously formed raising the pH. Electricity may be direct current or more preferably it is separated into individual pulses. Although the pulse voltage and/or current may vary preferably the pulse has a square shape. Specifically, at the initiation of the pulse voltage rises instantaneously to its peak level, stays at the peak level for the pulse duration and then instantaneously drops to zero at the end of the pulse.

The extent of the pH change, and the volume in which it occurs, is related to the variables of the electrical voltage and amperage. These variables are preferably expressed as the charge density, and most preferably as amperage per square millimeter of electrode surface.

Variables of electrode shape, composition, surface texture and orientation all effect the charge density and generation of protons. Electrodes can be made of any conduction material, metal, gel or electrolytic solution and a vast range of possibilities are known in the art (Bockris J., Modern Electrochemistry 1 Ionics, Plenum Press New York, 1970), hereby incorporated herein by reference. Preferable metals are iridium, platinum, gold, stainless steel or tungsten, and most preferred is oxidized iridium as it forms hydrogen ions at a wide range of charge densities (Ballestrasse C. L. et al., Calculations of the pH changes produced in body tissue by a spherical stimulation electrode, Annals of Biomedical Engineering, (1985) 13:405-424), hereby incorporated herein by reference.

A non-limiting example of an anodal electrode is a spherical ball of oxidized iridium with a radius of 1 μm. Electrical stimulation is delivered by square wave pulse lasting 0.2 seconds and the current density is 4 mAmps/mm2. Under these conditions the neutral pH at the surface of electrode falls to pH 4. This is sufficient for the invention to directly translocate a clostridial neurotoxin light chain across cell membranes. The pH change is directly proportional to distance, with pH 5 at 1 μm from the electrode surface and no significant change in pH 4 μm away from the surface (Ballestrasse C. L. et al., *Calculations of the pH changes produced in body tissue by a spherical stimulation electrode*, Annals of Biomedical Engineering, (1985) 13:405-424), hereby incorporated herein by reference.

This non-limiting example is illustrative of an embodiment of electrical induced acidification when precise localization of acidity is preferred. Essentially, the acidity is produced adjacent to the electrode, therefore the clinician can control the tissue volume in which the acidity is produced.

In one non-limiting example, the metallic shaft of a hollow bore needle insulated on the exterior surface, except at the opening at the tip, is connected to the anode of an electricity source, while a distant cathode electrode is attached to the skin surface. The needle is attached to a syringe containing a protein of the invention and an acidic electrolytic solution. A current is passed (continuous or pulsed) through the needle electrode to form protons in the immediate area of the needle tip. As a result, the local area around the needle tip has the proper acidity to cause translocation. Even if the tissue has been injected with a protein that normally would not enter cells in the area upon injection, the electricity causes local acidity that allows translocation. As further illustration of the above embodiment of the invention, the same electrode surface described above is exposed at the very tip of a thin needle attached to a syringe containing a clostridial neurotoxin light chain in a physiological saline solution. A patient has severe recurrent epileptic seizures originating from a 1 $mm^2$ lesion on the surface of the cerebral cortex. During a neurosurgical procedure the lesion is exposed and the needle is placed into the lesion where 0.01 cc of clostridial neurotoxin light chain solution is injected simultaneously with one or more 0.2 msec anodal electrical pulses. The pulses generate protons and resultant requisite acidity in the lesion without disturbing brain tissue less than 1 mm away. Although clostridial neurotoxin light chains do not normally enter cells, including neurons, the invention causes them to translocate directly in the pathological neurons of the lesion. The ability of electricity to increase the local acidity in precisely localized target tissue is of critical importance in the CNS as so many vital structures are often adjacent to pathological lesions.

3.1.2 Direct Translocation of Wild Type Clostridial Neurotoxin

Wild type botulinum toxins naturally bind to cholinergic efferent neurons and epithelial cells where they are internalized by endocytosis. In contrast there are some low-affinity gangliosides on all neuronal membranes and, although botulinum toxin binds to these sites, it is not internalized under normal conditions (M. V. De Angelis et al.: *Anti-GD1a antibodies from an acute motor axonal neuropathy patient selectively bind to motor nerve fiber nodes of Ranvier,* 121 Journal of Neuroimmunology 79-82 (2001), hereby incorporated herein by reference. However, according to one embodiment of the invention exposure of the membrane bound botulinum toxin to an acidic extracellular environment, for example, a pH range from about 4.5 to 6, more preferably, a pH value of about 5 to 5.5 triggers direct translocation of the free light chain across the cell membrane. Thus, according to this embodiment of the invention, light chains are delivered into neurons that botulinum neurotoxin cannot normally enter, including sympathetic neurons and sensory neurons. Particularly notable are the subclass of sensory neurons that sense pain. As discussed in more detail below, this greatly increases the efficacy of regulated SNARE inhibitors to treat disease.

In contrast to botulinum toxin, tetanus toxin binds to and is internalized by all peripheral neurons. However, the internalized tetanus toxin is preferentially transported to the CNS where its selective block of inhibitory neurons causes excitation. Thus, according to another embodiment of the invention, where a decrease of peripheral neuron activity is beneficial, the tetanus toxin can be exposed to an acidic environment before it is internalized. Into endosomes. Exposing the bound tetanus toxin to an acidic extracellular environment, preferably from about 4.5 to 6, and more preferably from about pH 5 to 5.5 triggers direct translocation of the tetanus toxin light chain across the cell membrane. This demonstrates how the method of this invention changes the increased activity that normally occurs in neurons intoxicated with tetanus toxin into decreased activity.

Under ideal conditions clostridial neurotoxins bind and are internalized within seconds. However, in vivo conditions are rarely ideal. After injection, the neurotoxins must diffuse through tissue to reach their natural high affinity binding sites on the presynaptic membrane. Because the toxins are large molecules, this diffusion can be quite slow. Therefore, depending on the particular tissue, the time allowed from injection of toxin to acidification can vary from simultaneous administration to up to ten hours, although 2 hours is preferred, and 20 minutes is more preferable. The exact time varies with the specific tissue and mode of delivery. However, after endocytosis begins, the toxin is no longer exposed to the extracellular environment and, therefore, is less effected by extracellular acidification.

4. Encapsulation Vectors

In another embodiment of the invention, regulated SNARE inhibitors are translocated across the cell membrane by an encapsulation vectors. As used herein the terms "encapsulation vectors" or "vectors" mean pharmaceutical preparations that physically or chemically surround the regulated SNARE inhibitor and function to facilitate translocation. Preferably the regulated SNARE inhibitor is not covalently bonded to the vector. Both physical and chemical encapsulation vectors are suitable for use in the invention.

Examples of physical encapsulation vectors suitable for use in the invention include, without limitation, liposomes, niosomes, viruses and nanoparticles.

In one aspect of this embodiment, the encapsulating vesicle is a liposome. Liposomes are artificial vesicles with single or multiple membranes that encapsulate surround a bioactive cargo and deliver it to cells either by membrane fusion or endocytosis. The membranes are made from natural and synthetic phospholipids, glycolipids, and other lipids and may include cholesterol; charged species which impart a net charge to the membrane; and specific binding moieties on their surface; and other lipid soluble compounds which have chemical or biological activity.

Preferred liposomes for use in the invention can be triggered to release their contents or fuse in response to pH stimuli, as they can potentially respond to acidic environments in vivo. Such environments include those encountered in tumor tissue and primary endocytic vesicles. See e.g.,

*Hafez Tunable pH-Sensitive Liposomes Composed of Mixtures of Cationic and Anionic Lipids* 79 Biophysical Journal 1438-1446 (2000), hereby incorporated herein by reference.

Botulinum toxin free light chain can be delivered via liposomes to block in vitro neuromuscular transmission at nanomolar doses, Paiva A, Dolly J O. *Light Chain Of Botulinum Neurotoxin Is Active In Mammalian Motor Nerve Terminals When Delivered Via Liposomes* FEBS Lett. 1990 Dec. 17; 277(1-2): 171-4, hereby incorporated herein by reference; WO 03/101483A1, Pharmaceutical Preparation Of Botulinum Neurotoxin, Methods Of Synthesis And Methods Of Clinical Use, hereby incorporated herein by reference, discloses methods of producing liposomes containing botulinum toxin.

In one preferred embodiment of the invention, liposomes are used as a translocating agent to skin cells and certain liposomes are appropriate for transdermal drug delivery (see e.g., U.S. Pat. No. 5,190,762 Method Of Administering Proteins To Living Skin Cells, hereby incorporated herein by reference).

In another preferred embodiment, liposomes can deliver regulated SNARE inhibitors to cancer cells (Harrington K et al., *Liposomally Targeted Cytotoxic Drugs For The Treatment Of Cancer*, Journal of Pharmacy and Pharmacology 2002, 54: 1573-1600, hereby incorporated herein by reference).

In another aspect of this embodiment, the encapsulating vesicles are niosomes. Niosomes, which may be considered a special case of liposomes, are prepared from non-ionic surfactants such as polyoxyethylene alkylether, polyoxyethylene alkylester or saccharose diester, see e.g., Rentel C O et al: *Niosomes As A Novel Peroral Vaccine Delivery System* Int. J. Pharm. 1999 Sep. 20; 186(2):161-7), hereby incorporated herein by reference.

In another aspect of this embodiment, the encapsulating vesicles are viruses, protein or glycoprotein structures encapsulating regulated SNARE inhibitor. See e.g., Cullen, B. R. *Journey to the center of the cell.* Cell 105, 697 (2001), hereby incorporated herein by reference.

In another aspect of this embodiment, the encapsulating vesicles are nanoparticles. Nanoparticles are 10 to 1000 nm particles made from polymers with the bioactive agent embedded inside. A preferred embodiment are nanoparticles composed by polyDL-lactide-coglycolide. These particles enter into cells by non-specific pinocytosis. They escape from acidified endosomes into cytoplasm and slowly dissolve and release their bioactive cargo. The polymeric material dissolves into lactic and glycolic acids that are metabolized by the cell and eliminated. See e.g., Panyam J et al., *Rapid Endo-Lysosomal Escape Of Polydl-Lactide-Coglycolide Nanoparticles: Implications For Drug And Gene Delivery* FASEB J. (2002) 16, 1217-1226, hereby incorporated herein by reference; Labhasetwar, V. (1997) *Nanoparticles For Drug Delivery*, Pharm. News 4, 28-31, hereby incorporated herein by reference.

Chemical encapsulation vectors are molecules that bond to the regulated SNARE inhibitor either by covalent or non-covalent bonds and isolate the regulated SNARE inhibitor from the surrounding aqueous environment. By analogy an illustrative example of the concept is the wild type botulinum toxin as produced by Clostridia in contaminated food. Botulinum toxin A is actually produced by bacteria with a coating of protective proteins that surround the toxin. These proteins are thought to protect the toxin from the acidic environment of the stomach which can reach a pH of 2.0 and denature the toxin. Another example of a chemical vector are monoclonal antibodies that are produced to bind to various antigenic sites of a toxin. The monoclonal antibodies are designed to protect the toxin from the extracellular environment but dissociate from the toxin at the acidic pH such as found in endosomes and the methods of this invention, see e.g., Raso V et al., *Intracellular Targeting with Low pH-triggered Bispecific Antibodies* Journal of Biological Chemistry, 1997, 272:27623-27628, hereby incorporated herein by reference. Another chemical encapsulating vector is the protein transduction domain Pep-1, or its equivalent, that is disclosed below.

5. Translocation and Binding of Regulated SNARE Inhibitors by Way of Protein Transduction Domains In another embodiment, the invention relates to translocation of regulated SNARE inhibitors across cell membranes by way of protein transduction domains. Protein transduction domains are relatively short polypeptides that, generally, bind to cells non-specifically (i.e., do not differentiate between cell types). It is believed that the mechanism of action involves electrostatic attraction between cationic charged amino acids of the protein transduction domain and anionic charges on the cell surface. These cause non-specific binding and internalization. Although the mechanism by which the protein domain enters cells on its own is unclear, when conjugated to bioactive cargo it enters via endosomes. Acidification causes direct translocation across the membrane. See e.g., Leifert J and Whitton L: "*Translocatory Proteins*" and "*Protein Transduction Domains": A Critical Analysis of Their Biological Effects and the Underlying Mechanisms*, Molecular therapy, 2003, 8:13-20, hereby incorporated herein by reference; Lindsay M., *Peptide-Mediated Cell Delivery: Application In Protein Target Validation* Current Opinion in Pharmacology 2002, 2:587-594, hereby incorporated herein by reference; U.S. 2002/0098236A1, Transport Vectors, hereby incorporated herein by reference.

Studies of the minimum translocation region identified a positively charged section between amino acids 47 and 57, which was previously associated with DNA binding, Vives E, Brodin P, Lebleu B, *A Truncated HIV-1 Tat Protein Basic Domain Rapidly Translocates Through The Plasma Membrane And Accumulates In The Cell Nucleus*. J Biol Chem 1997, 272:16010-16017, hereby incorporated herein by reference. Similar studies of antennapedia, a Drosophila homeodomain transcription factor, identified a 16-amino-acid PTD derived from region 43-58, and also located within the DNA-binding third domain. Lindgren M et al., *Translocation Properties Of Novel Cell Penetrating Transportan And Penetratin Analogues.* Bioconjug. Chem. 2000, 11:619-626, hereby incorporated herein by reference. Since these initial observations, a host of short peptides have been identified and shown to rapidly translocate across membranes. However, conjugation and delivery of biological cargo has been predominantly performed using the peptides derived from TAT, antennapedia and transportan, a synthetic chimera derived from galanin and mastoparan (Pooga M, Hallbrink M, Zorko M, Langel U: *Cell Penetration By Transportan FASEB J* 1998, 12:67-77, hereby incorporated herein by reference. Comparison of the uptake rate by fluorescence resonance energy transfer (FRET) analysis showed that the uptake of all these protein transduction domains was essentially complete within 15-60 min.

A preferable protein transduction domain is Pep-1 marketed as Chariot™ (Active Motif, Carlsbad Calif.) Pep-1 binds to bioactive cargo via non-covalent interactions, functions like a chemical encapsulation to protect the cargo extracellularly and then can translocate bioactive cargo intracellular in vitro and in vivo with 65-90% efficiency Pep-1 is composed of 21 amino acids consisting of three domains: (1) a hydrophobic tryptophan-rich motif containing five tryptophan residues required for efficient targeting to the cell membrane and for forming hydrophobic interactions with proteins; (2) a hydrophilic lysine-rich domain (KKKRKV) derived from the nuclear localization sequence (NLS) of simian virus 40 (SV-40) large T antigen, required to improve intracellular delivery and solubility of the peptide vector; and (3) a spacer domain (SQP), separating the two domains mentioned above, containing a proline residue, which improves the flexibility and the integrity of both the hydrophobic and the hydrophilic domains (Morris M et al: *Peptide carrier for the delivery of biologically active proteins into mammalian cells,* 2001 19:1173-1176) Chariot™ User Manual (version A), hereby incorporated by reference herein, teaches how to combine Pep-1 with proteins prior to application to cells and is herein incorporated by reference in its entirety. In vivo use of Pep-1 in mammals is disclosed in, Aoshiba K, *Alveolar Wall Apoptosis Causes Lung Destruction and Emphysematous Changes* American Journal of Respiratory Cell and Molecular Biology. Vol. 28, pp. 555-562, 2003, hereby incorporated herein by reference.

According to this embodiment of the invention, protein transduction domains are particularly useful with certain regulated SNARE inhibitors, such as the free light chain (which do not contain the heavy chain binding region) of clostridial neurotoxins and the protein IgA protease, that normally do not bind efficiently, if at all, to cell membranes. The protein transduction domain assists in bringing such molecules across the cell membrane where they can perform their SNARE inhibiting function.

6. Methods for Drug Delivery to Minimize Production of Antibodies

Immunogenicity is a major problem for complex pharmaceuticals. If a pharmaceutical is antigenic (generates antibodies), the drug should be used as efficiently as possible, to minimize neutralizing antibodies.

Antibodies circulate through the circulation and pass into the extracellular fluids. In most tissues, of antibody levels in the extracellular fluids is approximately the same as in plasma, except for the cerebrospinal fluid where antibodies are removed by an active process. If antibodies against a particular drug exist, it is important to minimize the drug's exposure.

According to one embodiment of the invention, if antibodies exist or are generated in increased amounts, certain modifications are made in the molecule itself or in the method of delivery to minimize antibody production and, to the extent antibodies are present, to minimize exposure of the drug to these antibodies.

For example, the production of neutralizing antibodies can be mitigated by decreasing the amount of drug used for a given condition and administer the drug such that it binds to its target as quickly as possible, thereby minimizing the extra drug that diffuses away from the area.

In another embodiment of the invention, the acid mediated translocation described above helps accomplish all these goals. Acidic environments interfere with antibody function. Tumors and inflamed tissue are both tissues where antibody function is known to be impaired. Acid decreases the affinity of antibodies to antigens, perhaps by making conformational changes in both. Therefore, acid mediated translocation directly aids the injected drug in avoiding neutralizing antibodies. Similar conformational changes can be achieved with extracellular alterations in ionic strength, urea concentration, and other chemical manipulations well known to those skilled in the art.

In one embodiment, regulated SNARE inhibitors, particularly, clostridial neurotoxin, can be chemically altered to cover its antigenic sites, for example, by polyethylene glycolation (PEG). Polyethylene glycol is positioned at various points of the molecule that prevent antibodies from approaching close enough to bind without stopping the activity of the molecule. In experimental animals, modification of a Pseudomonas exotoxin-derived immunotoxin with monomethoxy-polyethylene glycol (mPEG) diminished immunogenicity 5- to 10-fold, prolonged circulation time and preserved its anti-tumor effect.

In another embodiment, the amino acids side chains of regulated SNARE inhibitors are altered. This is readily accomplished by one of skill in the art by adapting the methods disclosed in U.S. pat. Appl. Pub. 2002/0127247A1 (published Sep. 12, 2002), which is hereby incorporated herein by reference.

Another method of the invention for covering/blocking the antigenic sites is with antibodies that are released under acidic conditions, such as are found in the endosomes.

In another embodiment of the invention, regulated SNARE inhibitors, for example, clostridial neurotoxin, are enveloped in an immunoliposome that is internalized into the cell by endocytosis, and then merges with the membrane of the endosomes at acidic pH, thereby liberating its contents into the cytoplasm.

In still another embodiment of the invention, antibodies can be useful. That is, antibodies against the drug can be injected within a period of time before or after drug delivery thereby "soaking up" excess drug that might cause the induction of an immune response.

In yet another embodiment of the invention for mitigating antibody formation, the extracellular space and/or the circulation in the area is decreased to prevent delivery of antibodies. For example, limb can be elevated and a tourniquet applied. Cold and pressure both decrease circulation as well as extracellular volume in tissue. Vasoconstrictors can decrease circulation to very low levels, and tissues can tolerate this for an hour or more. Epinephrine and similar vasoconstrictors are useful for this purpose.

In another embodiment, other substances or molecules can be injected along with the drug to bind antibodies. Certain bacterial proteins bind antibodies, these include proteins A, G, L, M. In addition anti-idiotype antibodies can be injected with the drug, or at a minimum the Fab fragments. An excess of haptens can be injected to saturate antibody binding sites. Alternatively inactive drug or fragments thereof can be used. Of this embodiment of the invention an example is to inject tetanus toxoid along with tetanus toxin.

*Staphylococcus aureus* protein A binds to IgG via surfaces in the Fc-fragment of the heavy chain of the IgG-molecule, however, protein A lacks the ability to bind to human IgG3. Protein G binds to heavy chains in human IgG and to all four of its subclasses. Protein H binds to the Fe-fragment in IgG from human beings, monkeys and rabbits. Protein G binds to heavy chains in human IgG and to all four of its subclasses. Protein M binds to the Fe-fragment in IgG from humans, monkeys, rabbits, goats, mice and pigs (PCT/SE91100447), hereby incorporated herein by reference. Protein L binds to the light chains in immunoglobulins from all of the classes of G, A, M, D and E is known. See e.g., U.S. Pat. No. 4,876,194 (issued Oct. 24, 1999), which is hereby incorporated herein by reference. U.S. patent application publication no. 2003/0027283A1 (published Feb. 6, 2003), which is hereby incorporated herein by reference, discloses a recombinant protein L that can be used for above purposes. In addition, in some autoimmune diseases, there is a great need to reduce or eliminate serum antibodies, and this application suggests that this recombinant protein L may be of value. The above-mentioned proteins are used in the analysis, purification and preparation of antibodies from solution ex vivo for diagnostic and biological research and have not been used in vivo.

Alternatively monoclonal antibodies can be produced that bind human antibodies. EP0163141131, Monoclonal anti-human IgG antibody and process for preparing the same, hereby incorporated herein by reference, teaches how these can be prepared, although the purpose in the disclosed invention is for these antibodies to be part of an in vitro diagnostic test. If antibodies are to be used in humans they must be "humanized", i.e., have any foreign antigens removed. Recombinant techniques allow for the design and mass production of various size humanized monoclonal antibodies against selected antigens. For the purposes of the present invention the entire antibody against human antibody need not be used. Instead, only the binding fragment with specificity against the binding site of human antibodies is necessary.

7. Methods of Administration of Toxins Formulations of the Invention

Preferably, the regulated SNARE inhibitors used according to the methods of the invention are administered by local delivery or administration by methods well known in the art. Suitable local administration methods include intraperitoneal, injection into an organ, intramuscular, intraventricular, subcutaneous, topical, sublingual, nasal, parenteral, ocular, intradermal, subcutaneous, and topical administration modes.

Preferably, the regulated SNARE inhibitors are administered in pharmaceutically acceptable formulations. Preferably, such formulations are sterile. Pharmaceutically acceptable methods and formulations are well known in the art, for example: parenteral injection and formulations are discussed in 2 Remington: The Science and Practice of Pharmacy 1524-1548 (Alfonso R. Gennaro ed., 19th ed., 1995), hereby incorporated herein by reference; topical formulations and administration is described in 2 Remington: The Science and Practice of Pharmacy 866-885 (Alfonso R. Gennaro ed., 19th ed., 1995), hereby incorporated herein by reference; administration by way of solutions, emulsions and extracts is discussed in 2 Remington: The Science and Practice of Pharmacy 1495-1523 (Alfonso R. Gennaro ed., 19th ed., 1995), hereby incorporated herein by reference; administration by way of ophthalmic formulations is discussed in 2 Remington: The Science and Practice of Pharmacy 1495-1523 (Alfonso R. Gennaro ed., 19th ed., 1995), hereby incorporated herein by reference; administration by way of aerosols is discussed in 2 Remington: The Science and Practice of Pharmacy 1676-1692 (Alfonso R. Gennaro ed., 19th ed., 1995), hereby incorporated herein by reference; administration by way of powders is discussed in 2 Remington: The Science and Practice of Pharmacy 1598-1614 (Alfonso R. Gennaro ed., 19th ed., 1995), hereby incorporated herein by reference.

Regulated SNARE inhibitors can be administered by standard techniques well known in the art, for example, without limitation, in formulations, such as solutions, powders, biogels, polymers, microparticles, liposomes or micelles.

7.1.1 Administration by Local Injection 7.1.1.1 Application of Clostridial Neurotoxins along Axons Notably, both botulinum and tetanus toxin normally bind and are internalized into neurons at the synapse, the point of contact between the neuron and its target cell. This area contains the regulated SNARE protein mediating neurotransmission. Therefore, at least for botulinum toxin, its internalization in this area and the subsequent translocation of the light chain from the endosome places the light chain in close proximity to the regulated SNARE proteins. One reason that clostridial neurotoxins preferentially bind to this area is that the presynaptic membrane contains very high concentrations of ganglioside GT-1. However, GT-1 ganglioside or others that have slightly less affinity are present along the entire length of peripheral axons, albeit at much lower concentrations than at the presynaptic membrane. It has been shown that both botulinum and tetanus toxin bind to these regions but are not internalized. See e.g., Angelis M. V. et al., *Anti-GD1a Antibodies From An Acute Motor Axonal Neuropathy Patient Selectively Bind To Motor Nerve Fiber Nodes Of Ranvier* Journal of Neuroimmunology 121 (2001) 79-82, hereby incorporated herein by reference. However, if the bound clostridial neurotoxins are exposed to high acidity they would translocate their light chains into the axons.

Neurons form their proteins at the cell body and transport them through the axon the entire distance from the axon to the synapse. It is known that among the proteins transported in this manner are the regulated SNARE proteins. See e.g., Diefenbach R. J. et al., *The Heavy Chain Of Conventional Kinesin Interacts With The Snare Proteins SNAP25 And SNAP23*, 41 Biochemistry 14906-14915 (2002), hereby incorporated herein by reference. Therefore translocation of clostridial neurotoxin light chains, at any point along the axon, allows them to cleave the transported regulated SNARES thereby rendering them inactive. In many clinical situations the tissue that would benefit from injection of a regulated SNARE inhibitor contains other nerve elements or cells that perform regulated SNARE exocytosis. Therefore it is preferable that if the nerve in need of inhibition can be easily accessed at any point along its route, it can be selectively inhibited. As an illustrative example, a patient has a cancer involving a bone of the left foot and is in need of analgesia. Administration of a regulated SNARE inhibitor can be done in and around the bone cancer to block pain fibers however, an undesirable side effect is that nerves to muscles in the area are also inhibited and the muscles are temporarily paralyzed. Although motor and sensory nerve fibers are mixed in peripheral nerves they separate prior to entering into the spinal cord. Specifically, motor fibers enter more anterior than sensory fibers, they divide into the ventral and dorsal roots of the spinal nerve from that segment of spinal cord. At the dorsal root the sensory fibers can be accessed and blocked without effecting the motor nerve, thereby avoiding paralysis. This shows how the methods of this invention allow selective inhibition of nerves that innervate a tissue. Numerous other situations where this is of value would be evident to a person skilled in the art, and further detailed examples are provided below.

In one embodiment of the acid mediated transport methods of the invention, regulated SNARE inhibitors are injected from about one-second to about two hours prior to acidification, thereby allowing regulated SNARE inhibitors to bind prior to translocation. In another embodiment, injection of regulated SNARE inhibitors is performed simultaneously with injection of an acid formulation, thereby causing more general and non-specific binding. The injection of acid solution could also precede injection of the protein of the inventions.

In one embodiment, regulated SNARE inhibitors or formulations thereof, are administered locally by injecting according to standard techniques. Local injection of regulated SNARE inhibitors can be performed by needle injection, needleless pressure injection, biodegradable and non-degradable implants and implantable pumps. Further non-limiting examples are to incorporate the SNARE inhibitors onto coatings or parts of intravascular stents, implanted artificial or transplanted organs or tissues.

For local injection, the compounds of the invention can be formulated in physiologically compatible aqueous solutions, such as Hanks's solution, Ringer's solution, or physiological saline buffer.

Another embodiment of the invention is to inject the protein of the invention into an enclosed space such as pleural cavity, joint spaces, gastrointestinal, genitourinary or reproductive organs, lymphatics, and blood vessels. Another embodiment of the invention is to inject the protein of the invention into tissues or organs of relatively homogenous cell types. Such organs would include the central nervous system, peripheral nerves, endocrine glands, liver and pancreas, bone marrow, cartilage, connective tissue, fat, nasal cavity and nasal sinuses, and pathologic material such as benign and malignant tumors. In another embodiment of the invention, the toxins of the invention are injected into vessels supplying specific areas, lymphatics, cerebrospinal fluid, anterior or posterior chamber of the eye, the cochlea or middle ear, synovial or pleural cavities.

7.1.2 Topical Administration

As used herein, the term "topical administration" or "topical delivery" means intradermal administration of a regulated SNARE inhibitor by administration of the regulated SNARE inhibitor or a composition comprising the regulated SNARE inhibitor to intact skin. For example, by rubbing a composition of the invention onto an area of intact skin or by placing an intradermal patch comprising a composition of the invention onto an area of intact skin. The term "topical composition" means a pharmaceutical composition designed for topical administration and containing a pharmaceutical.

Regulated SNARE inhibitors can be applied topically in intradermal or transdermal formulations, such as solutions, creams, emollients, ointments, patches, aerosols, sprays, and mists. Processes to spread diffusion across mucosal or skin barriers can be used, for example by use of liposomes or iontophoresis. One embodiment of the invention is to administer regulated SNARE inhibitors in topical, slow-release solids, gels or polymers by application to the skin or mucus membranes. Specific embodiments include biodegradable contact lens, a coated or biodegradable implant or stent for the nose, sinuses, Eustachian tube or in the form of a myringotomy tube, intrauterine device, or indwelling catheter. Further examples are obvious to those skilled in the art.

7.1.3 Activation of Amphipathic Proteins or Their Coniueates

According to one embodiment of the invention, regulated SNARE inhibitors can be used in an inactive or wild-type form. In another embodiment, regulated SNARE inhibitors can be used in a form that is activated at body temperature upon exposure to typical in vivo conditions or the specific local conditions found in specific tissues. In still another embodiment, regulated SNARE inhibitors can also be designed such that under certain conditions they are activated. For example, activation by external signal or external or internal energy sources such as electrical current, microwave, ultrasound, or hypertherma or hypothermia.

7.2 Dosages

Pharmaceutical preparations suitable for use with the present invention include compositions wherein the regulated SNARE inhibitors are present in effective amounts, i.e., in amounts effective to achieve the intended purpose, for example, modulation of cellular function or treatment of disease. Of course, the actual amounts of the regulated SNARE inhibitors effective for a particular application will depend upon a variety of factors including, inter alia, the disease being treated, the age and weight of the subject and, where appropriate, the judgment of the prescribing physician. Determination of effective amounts is well within the capabilities of those skilled in the art, especially in light of the detailed disclosure herein.

The regulated SNARE inhibitors can be locally administered in any manner that achieves the requisite therapeutic or prophylactic effect. Therapeutically or prophylactically effective doses of the regulated SNARE inhibitors can be determined from animal or human data. The applied doses can be adjusted based on the relative bioavailability, potency and in vivo half-life of the administered regulated SNARE inhibitors. Adjusting the dose to achieve maximal efficacy in humans based on methods that are well-known is well within the capabilities of the ordinarily skilled artisan.

Typically, dosages and therapeutically effective amounts range from about 0.001 units to about 10,000 units of the regulated SNARE inhibitor, preferably, from about 0.1 units to about 1000 units, more preferably, in the range of about 1 units to about 100 units. Typically, each dose is administered once a day to once every 3 years, preferably, once a week to once a year, more preferably once a month to once a year.

8. Treatment of Disease Using the Methods of the Invention to Deliver Regulated SNARE Inhibitors The methods, compositions, and formulations of the invention are useful for treatment and/or prevention of disease in mammals.

The methods, compositions, and formulations are useful to treat all disease, conditions, and symptoms disclosed in WO 02/00172, to Ira Sanders, PCT/US01/20523 (published Jan. 3, 2002), which is hereby incorporated herein by reference, and the methods and formulations described therein can be adapted in the present invention.

In one embodiment, the methods of the invention are directed treatment, reduction of symptoms, and/or prevention of disease in mammals using acid mediated translocation of regulated SNARE inhibitors. In another embodiment, the methods of the invention are directed to treatment, reduction of symptoms, and/or prevention of disease in mammals by translocation and binding of regulated SNARE inhibitors by way of protein transduction domains. In yet another embodiment, the methods of the invention are directed to treatment, reduction of symptoms, and/or prevention of disease in mammals by translocation and binding of regulated SNARE inhibitors by way of encapsulation vectors.

The methods of the invention are useful for the treatment, reduction of symptoms, and/or prevention of achalasia, anal fissure, anismus, blepharospasm, cerebral palsy, cervical dystonia, cervicogenic headache, hemifacial spasm, dyshidrotic eczema, dysphagia, dysphonia, esophageal dysmotility, esophageal muscular ring, esotropia (infantile), eyelift, facial myokemia, gait disturbances (idiopathic toe-walking), generalized dystonia, hemifacial spasm, hyperfunctional facial lines (glabellar, forehead, crow feet, down-turned angles of the mouth), hyperhidrosis, incontinence (spinal cord injury), migraine headache, myoclonus, myofascial pain syndrome, obstructive urinary symptoms, pancreas divisum pancreatitis, Parkinson's disease, puborectalis syndrome, reduction of surgical scar tension, salivary hypersecretion, sialocele, sixth nerve palsy, spasticity, speech/voice disorders, strabismus, surgery adjunct (ophthalmic), tardive dyskinesia, temporomandibular joint disorders, tension headache, thoracic outlet syndrome, torsion dystonia, torticolis, Tourette's syndrome, tremor, whiplash-associated neck pain, pain, itching, inflammation, allergy, cancer and benign tumors, fever, obesity, infectious diseases, viral and bacterial, hypertension, cardiac arrhythmias, vasospasm, atherosclerosis, endothelial hyperplasia, venous thrombosis, varicose veins, apthous stomatitis, hypersalivation, temporomandibular joint syndrome, sweating, body odor, acne, rosacea, hyperpigmention, hypertrophic scars, keloid, calluses and corns, skin wrinkling, excessive sebum production, psoriasis, dermatitis, allergic rhinitis, nasal congestion, post nasal drip, sneezing, ear wax, serous and suppurative otitis media, tonsil and adenoid hypertrophy, tinnitus, dizziness, vertigo, hoarseness, cough, sleep apnea, snoring, glaucoma, conjunctivitis, uveitis, strabismus, Grave's disease, asthma, bronchitis, emphysema, mucus production, pleuritis, coagulation disorders, myeloproliferative disorders, disorders involving eosinophils, neutrophils, macrophages and lymphocytes, immune tolerance and transplantation, autoimmune disorders, dysphagia, acid reflux, hiatal hernia, gastritis and hyperacidity, diarrhea and constipation, hemorrhoids, urinary incontinence, prostatic hypertrophy, erectile dysfunction, priapism and Peyronie's disease, epididymitis, contraception, menstrual cramps, preventing premature delivery, endometriosis and fibroids, arthritis, osteoarthritis, rheumatoid, bursitis, tendonitis, tenosynovitis, fibromyalgia, seizure disorders, cerebral palsy, spasticity, headache, and neuralgias.

In a preferred embodiment, the methods of the invention are useful for the treatment, reduction of symptoms, and/or prevention of pain or inflammation; migraine headaches; allergy; cystic fibrosis; disease related to adipose tissue; viral infection; cancer; fever; sweating, eccrine, and apocrine; disease related to or associated with holocrine secretions and acne; disease relate to mucous secretion; prostatic hypertrophy; diseases treatable by gene therapy; disease of the veins, such as venous stasis, varicose veins and hemorrhoids; high blood pressure. The methods of the invention are also directed to use of regulated SNARE inhibitors simultaneously as a therapeutic agent and as a vaccine.

In another embodiment, the invention is directed to preparation of a medicament or pharmaceutically acceptable formulation, preferably a medicament or pharmaceutical acceptable formulation suitable for local delivery, comprising a therapeutically effective amount of a regulated SNARE inhibitor for use in the methods of the invention.

8.1. Pain and Inflammation 8.1.1 Pain

In one embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to treat, reduce the symptoms of, and/or prevent pain in mammals, and the related process of inflammation, which causes pain.

Pain is a noxious sensation mediated by a special class of neurons called nociceptors. The majority of these nociceptors are unmyelinated C fibers and the thin myelinated A delta fibers, which are concentrated in the skin and mucosa. Nociceptors have membrane receptors that respond to heat, acid, and a wide variety of endogenous bioactive substances secreted by other neurons surrounding tissue cells and from white blood cells that migrate out of the blood stream to the involved area.

Unmyelinated C fibers are unusual in that the terminal axons of single neuron cover a relatively wide area, up to several centimeters in skin. Stimulation of a single terminal is conveyed directly to the other terminal axons of the same neuron as well as sent back to the CNS. The direct transmission of signals from one terminal axon to another is called axon-axonal reflex and plays an important role. These C nociceptors have the ability to release neuropeptides thereby causing an inflammatory reaction in surrounding areas not involved in the original painful stimuli. Neuropeptides released by nociceptors include substance P and CGRP. Substance P has numerous effects, it can stimulate pain sensation in other nociceptors and activate local tissue cells called mast cells that contain a wide variety of bioactive substances that contribute to inflammation and further pain. CGRP is a powerful dilator of blood vessels and causes increased circulation to the area. The resultant reaction amplifies the original noxious insult by neural mechanism and by activation of surrounding cells. The clinical signs of inflammation have been described for centuries as heat (due to increased circulation), swelling (secondary to fluid passing from local blood vessels into the tissue), redness (due to the increased blood circulation), and pain (noxious sensation from the original insult as well as the numerous bioactive substances released in the area).

Sensory neurons have their cell bodies in ganglia outside the central nervous system and have two axons. One axon courses down peripheral nerves to be distributed to innervate tissue, and the second axon passes to the spinal cord. Activation of the membrane receptors of the terminal axons of the nociceptors initiates a neural signal that passes along the length of the neuron to secondary relay neurons in the spinal cord and brainstem. The principal neurotransmitters at the synapses between nociceptor neuron and the relay neuron are substance P, glutamate, CGRP and neuropeptide Y. Some processing of the signal occurs at this synapse that either inhibits or enhances the signal. In addition, under certain conditions the signal can elicit local reflexes at the spinal-cord level that are sent through efferent neurons to the periphery tissue, further amplifying the reaction.

As pain is a symptom of many different diseases and perhaps the single largest cause of human suffering it has been a priority for therapeutic intervention. Therapeutic interventions have been devised to intervene at many points from the peripheral tissue to brain. Examples of treatments for treating pain at the tissue level include steroids and non-steroidal anti-inflammatory drugs (NSAIDS) such as aspirin; and in the CNS the principle drugs used are narcotics such as Demerol. Aspirin blocks production of prostaglandins, an important mediator of pain and inflammation produced by tissue cells. Aspirin is effective for mild pain from some sources but does relief strong pain. Moreover, aspirin is associated with significant side effects, it inhibits blood clotting, thereby making the patient susceptible to spontaneous bleeding, it irritates the gastrointestinal tract and can cause gastritis and ulcers, and chronic use can cause tinnitus. Narcotics are the primary treatment for severe pain. Narcotics work by inhibiting the transmission of pain signals in the CNS. However, narcotics have numerous side effects: respiratory depression; clouded sensorium; and addiction. In practice the exaggerated fear of addiction causes physicians to routinely under-dose patients, and this is a major cause of suffering in the patient population most in need of pain relief.

In their wild type form, the *Clostridia tetani* have some analgesic and anti-inflammatory properties with tetanus toxin having more effects then botulinum toxin. In clinical practice, wounds infected solely by *Clostridia tetani* are not painful. In fact, some patients are unaware they have an infection until the onset of tetanic symptoms. Tetanus toxin is known to bind to and be internalized by all nerves including sensory nerves such as the nociceptors. Finally, another important difference between tetanus toxin and all the botulinum toxin serotypes is that tetanus toxin can enter into and inhibit white blood cells such as macrophages that are drawn to injured tissue and greatly amplify the inflammatory response. For these reasons, tetanus neurotoxin is more versatile then botulinum toxin as an analgesic or anti inflammatory agent, although it is not ideal as most of the toxin is transported by nerves out of the area. WO 02/00172: Methods for using tetanus toxin for beneficial purposes in animals (mammals), hereby incorporated herein by reference teaches the use of tetanus toxin for the treatment of pain and inflammatory conditions.

It is believed that botulinum toxin has a significant effect on pain that is caused by muscle spasms, this being secondary to the inhibition of muscle contraction. In addition, injections of botulinum toxin into the temporalis and frontalis muscles has been shown to be effective in the treatment of headache (Binder W. et al., (2000) *Botulinum toxin type A (Botox®) for the treatment of migraine headache*, Otolaryngol Head and Neck Surg 123: 169-176, hereby incorporated herein by reference). However, based on animal experiments it has also been claimed that botulinum toxin has an effect on inflammatory evoked pain (U.S. Pat. No. 6,063,768: Application of botulinum toxin to the management of neurogenic inflammatory disorders), and chronic pain syndromes (U.S. 2004/0028706A1: Neuralgia pain treatment by peripheral administration of a neurotoxin), hereby incorporated herein by reference. Borodic teaches against the use of botulinum toxin due to paralysis of muscles surrounding the injection site, see e.g., U.S. Pat. No. 6,429,189: Cytotoxin (Non-Neurotoxin) For The Treatment Of Human Headache Disorders And Inflammatory Diseases, hereby incorporated herein by reference). Moreover, controlled experiments in humans fail to show any direct effect of botulinum toxin on pain (Blersch W. et al., (2002) *Botulinum Toxin A And The Cutaneous Nociception In Humans: A Prospective, Double-Blind, Placebo-Controlled, Randomized Study*, J. Neurol. Sci., 205:59-63), hereby incorporated herein by reference. In fact there are receptors for acetylcholine on nociceptors, and stimulation of these receptors decreases pain (Dusser G, et al., *Cholinergic Modulation Of Nociceptive Responses In Vivo And Neuropeptide Release In Vitro At The Level Of The Primary Sensory Neuron*, Pain 107 (2004) 22-32), hereby incorporated herein by reference.

Due to the shortcomings of wild type *Clostridia tetani* investigators have developed modified forms of the toxins that bind specifically to sensory neurons. to nociceptors U.S. Pat. No. 5,989,545: Clostridial Toxin Derivatives Able To Modify Peripheral Sensory Afferent Functions, hereby incorporated herein by reference, discloses a modified botulinum toxin in which the binding domain is replaced by a compound that binds to sensory neurons. Therefore alight chain is introduced to nociceptor neurons for the purposes of blocking the synapse between the nociceptor neuron and the first relay neuron in the CNS. WO/0057897A1: Use Of A Lectin Or Conjugates For Modulation Of C-Fibre Activity, hereby incorporated herein by reference, specifically discloses the use of a lectin to replace the wild type binding domain, as lectins have specific affinity for the nociceptor c fibers. In U.S. 2003/0165541A1: Methods for treating inflammation pain, hereby incorporated herein by reference, the specific target of the toxin is changed from a neuron to a non-neuronal cell that contains receptors for substance P. Although many different cell types contain substance P receptors, those contributing to the inflammatory response are mast cells and endothelial cells. Type TC mast cells (those containing the enzymes trypsin and chymase) are filled with large vesicles containing many inflammatory bioactive substances. When properly stimulated they release all these substances in a rapid process called degranulation. However, this degranulation does not utilize regulated SNAREs and therefore this function would not be impaired by CNT.

Preventing the vesicle mediated replacement of cell membrane at the sensory endings of the nociceptors prevents the replacement of nociceptors membrane receptors and cause their depletion and the neuron stops responding to pain. Stopping neurotransmitter release at the synapse between the primary and projection neuron blocks the transmission of pain. Furthermore, any process that interferes with the action potentials propagating along the axon will also block pain signals.

According to the invention, pain is blocked at various points along the pathway described above by locally administering regulated SNARE inhibitors according to the methods of the invention to effect efficient cell membrane binding and/or translocation.

In one example of this embodiment, a male patient experiences pain in the elbow region. To alleviate this pain a needle is passed through the skin above the elbow and small continuous pulses of electricity are applied through the tip of the needle. When the needle tip touches the nerve supplying the area from which pain is experienced he feels a tingling in the area that the nerve distributes to, and informs the clinician. The clinician advances the needle slightly until the needle tip is under the perineurium of the nerve. The clinician slowly infuses 5 ml of normal saline containing 10 units of tetanus neurotoxin. The clinician waits for 2 minutes to allow the solution to diffuse along the nerve and for the tetanus neurotoxin to bind. As the pain neurons are mostly unmyelinated C fibers, their entire axonal membrane is exposed for the tetanus neurotoxin to bind. In contrast, the myelinated fibers are covered by Schwann cells and only a small percentage of their membrane is exposed at the nodes of Ranvier. After the waiting period, a continuous current of 1 amp is passed through the needle tip in a pulse lasting 10 seconds. A pH below 6.0 is generated in the region of the nerve around the needle tip. This causes the tetanus neurotoxin to preferentially translocate its light chains into the neurons. These light chains then diffuse proximal and distal over the next 24 hours to reach presynaptic membranes where they block vesicle release, thereby blocking pain sensation.

As a further example of blocking pain, botulinum neurotoxin C2 can be translocated across axon membranes to stop the propagation of axon action potentials. Botulinum neurotoxin C2 exists as separate heavy and light chains that bind at the cell surface and are internalized into endosomes. After acidification, the C2 light chain translocates into the cytoplasm. C2 disassembles actin, therefore, disrupting the cytoskeleton and transport. Injection of Acid/C2 under the epineural of a peripheral nerve would establish conditions for translocation of the C2 light chain into axons; disruption of tubules causes a local area where action potentials do not propagate thereby blocking pain sensation.

As a further example, a 40-year-old female has rheumatoid arthritis with severe left knee pain. The clinician injects the serosal joint cavity with a solution of 30 units of botulinum neurotoxin dissociated light and heavy chains with anthrax protective antigen (the amphipathic component of anthrax toxin) in an acidic carrier solution. The botulinum neurotoxin light chains are thereby translocated into the nociceptive neurons and cause them to stop recycling membrane receptors thereby relieving the pain.

8.1.1.1 Pain from Migraine Headaches

In yet another embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to treat, reduce the symptoms of, and/or prevent the pain associated with migraine headaches in mammals It is thought that the etiology of migraine and other headaches is a neurogenic allergic reaction. The initial brief vasoconstriction is followed by a vasodilation. The vasoconstriction causes the aura, a brief neurological aberration. The following vasodilation is painful. It has been shown that neural activity alone can cause mast cell degranulation around the dura. The nerve supply of the cerebral vessels through autonomic neurons in the sphenopalatine ganglion, these join the carotid arteries when they pas through the skull base. Some treatments of migraine use ergotamines, a substance that causes prolonged vasoconstriction. Blocking the neurogenic pathway can treat the migraine.

In one example of this embodiment of the invention, a 30-year-old female with recurrent left-sided migraine headaches is injected with 10 units of botulinum neurotoxin A into her pterygopalatine space by passing a 27 gauge needle 1.5 inches through the sphenopalatine canal and injecting the botulinum neurotoxin in 3 ml of saline carrier solution. Patient reports a resolution of her migraine for 3 months.

8.1.2 Inflammation and Associated Pain

In one more embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to treat, reduce the symptoms of, and/or prevent inflammation and the pain associated with inflammation in mammals.

Regulated SNARE inhibitors are useful to treat inflammation. For example, U.S. Pat. No. 6,063,768, hereby incorporated herein by reference, discloses application of botulinum toxin to manage neurogenic inflammatory disorders, especially in rheumatoid joints, which is hereby incorporated by reference herein. However, such methods suffer from lack of efficiency of cell membrane translocation and/or binding.

In one example of this embodiment of the invention, a 60 year old female has severe rheumatoid inflammation in her right knee. She undergoes injection of 20 units of anthrax protective antigen/lethal toxin in 2 ml normal saline into the knee. The following day the inflammation has subsided.

8.2 Allergy

In one embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to treat, reduce the symptoms of, and/or prevent allergy in mammals.

The methods of the invention are useful to treat, for example, allergic conditions, such as allergy related rhinitis, asthma, conjunctivitis, gastroenteritis, serous otitis, sinusitis and dermatitis, and related conditions, such as infectious sinusitis and otitis media that occur secondary to allergy induced mucosal swelling. According to the methods of the invention, regulated SNARE inhibitors are administered to the body structure and/or the nerves and nerve ganglia supplying these structures. In the case of botulinum neurotoxin C2 the target is not the neuron but the mast cell.

Common to allergies is the involvement of the IgE class of antibody. Individuals are not born with allergies, rather, they acquire them by exposure to allergens. The steps of the IgE allergic reaction are sensitization upon first exposure to the allergen, and then the allergic response to subsequent exposures. The allergic response consists of an immediate and delayed response referred to as the early and late phase responses respectively. In atopic individuals, those prone to allergies, the initial exposure to an antigen results in the production of IgE antibodies that specifically recognize that allergen. This process is called sensitization.

The early-phase response (ERP) is the immediate reaction that occurs within minutes of exposure to an allergen. IgE are bound to the surface of a neuroimmune cell called the mast cell (in the circulation these cells are called basophils). Sufficient numbers of bound IgE antibodies that react with an allergen causes the mast cell to release contetanus neurotoxin of secretory vesicles, a process known as degranulation. The secretory vesicles contain histamine and other stored substances such as nerve growth factor (NGF). In addition, the mast cell and T cells immediately begin manufacturing leukotrienes, cytokines, enzymes and substances that activate blood platelets and attract secondary cells to the area. Eosinophils produce major basic protein, eosinophil cationic protein, leukotrienes and nerve growth factor. TH2 lymphocytes release cytokines that promote further IgE production and eosinophil chemo attraction, and increased numbers of mast cells. The sensory nerve stimulation causes reflexes that are designed to aid in defending the tissue. These reflexes are often a larger problem then the local allergic response. Reflexes can range from large gross motor actions to regional afferent and efferent arcs or even local axon-axonal reflexes involving a single neuron.

Some reflexes recruit major motor actions that are well recognized. In the nose sneezing is a reflex attempt to expel unwanted material and coughing is the equivalent response in the lungs.

Regional reflex arcs involve the sensing of the stimulus by the sensory neuron, the transfer of the message to the ganglia and the central nervous system and an efferent response via autonomic neurons. Reflex excitation by the autonomic nervous system directly causes mast cell to degranulate, thereby spreading the reaction. In addition, these reflexes control a variety of other functions. In the nose, these reflexes cause increased mucus production, increased cilia movement, and congestion. In the lungs, reflexes cause bronchospasm, increased mucosal congestion, and production of airway secretions. In the GI tract, reflexes cause dysmotility, mucosal congestion, and secretions. In the skin, the reflexes cause swelling and itching.

Finally, there are local axon-axonal reflexes in sensory nociceptive nerve fibers. Allergic stimulation of a single neuron causes release of mediators from other axons of the same neuron.

In chronic allergic stimulation, the mast cells and eosinophils releases nerve growth factor that causes growth of the nerves in the region. Thereby allowing for increased neural responses and hyper reactivity.

There is a great need for an effective treatment for allergic disorders. It has long been thought that the allergic reaction involved only histamine release by mast cells. Therefore, first line therapy for allergy was antihistamines, or more recently the non-sedating antihistamines. Other therapies are directed to block the effects of the mast cell secretions with adrenergic agonists. It is not obvious to those skilled in the art that a central role in allergic disorders involves the autonomic nervous system and that this nerve activity can be blocked by regulated SNARE inhibitors for a beneficial effect.

In one embodiment of this aspect of the invention, upon local administration, regulated SNARE inhibitors interfere with the allergic process by: (1) Directly blocking degranulation by the mast cell (principally botulinum neurotoxin C2), (2) Block the degranulation of the mast cell induced by autonomic nerve activity. (3) Decrease humoral release during axonal reflexes. (4) Decrease the parasympathetic effector arm of reflex allergic responses (5) Decrease the increased tonic activity of the autonomic systemic that is related to prior allergic reactions. (6) Decrease the nerve enlargement induced by nerve growth factor released during allergic reactions. (7) Reverse certain complications of allergic reactions such as mucosal thickening by decreasing autonomic nerve activity. (8) Combinations of botulinum neurotoxin and tetanus neurotoxin can have a synergistic effect: for example, botulinum neurotoxin can block parasympathetic nerves while tetanus neurotoxin can excite sympathetic nerves thereby causing decongestion.

In one example of this embodiment of the invention, a 30-year-old male has seasonal allergic rhinitis. In May, prior to pollen formation, he has 30 units of botulinum neurotoxin topically applied in each nostril. Specifically, the botulinum neurotoxin is absorbed onto cotton pledgets that are placed into each nasal cavity for one hour. In the following months, the symptoms he normally experiences, itching, sneezing and nasal congestion are significantly reduced. Alternatively, the same patient can be treated with 20 units of botulinum neurotoxin and 10 units of tetanus neurotoxin to combine an anti-parasympathetic effect with a sympathomimetic effect. Alternatively, if decongestion is desired, 10 units of tetanus neurotoxin can be topically applied. In another embodiment, 1 unit of recombinant DNA coding for tetanus neurotoxin is pressure injected across the nasal mucosa to transfect mucosal cells. These cells then express the tetanus neurotoxin for months.

In another embodiment the light chains from 30 units of botulinum neurotoxin/E in 10 ml saline are sprayed into each nostril by an atomizer. A thin electrolytic membrane is placed over the mucus membranes of each inferior turbinate. Electrical current is applied across the biogel and its mucosal side becomes acidic thereby allowing translocation of the botulinum neurotoxin/E light chins into mucosa, mast cells and neurons.

8.3 Cystic Fibrosis

In yet another embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to treat, reduce the symptoms of and/or prevent cystic fibrosis and related conditions.

Regulated SNARE inhibitors can be incorporated into cell membranes to control the interaction of the cell with its environment, for example, transporter and signal transduction membrane proteins, identifying antigens, and others. An example of a disease that can be treated using this embodiment of the invention is cystic fibrosis cystic fibrosis is a condition in which a membrane transport protein is missing in respiratory epithelial mucosal cells. As a result, the respiratory secretions are excessively thick. The conjugate to the amphipathic proteins might be the missing transport protein.

8.4 Disease Related to Adipose Tissue

In still yet another embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to treat, reduce the symptoms of, and/or prevent disease related to adipose tissue in mammals.

Increased adipose tissue is a major health problem in industrialized societies. Decreased caloric intake is associated with fewer chronic diseases, such as diabetes and hypertension, as well as a longer life span. Also, the reduction of or repositioning of fat deposits is desirable for cosmetic reasons. In order for adipocytes to take up glucose from the circulation, cell vesicles containing the glucose transporters (GLUT) add the enzyme to cell membrane. The increased uptake of glucose is converted into fat. Tomori et al. showed that botulinum neurotoxin could prevent the docking of these vesicles in adipocytes permeabilized with streptolysin-O. Chen demonstrated that adipocytes had SNAP-23, a SNAP isoform that is not cleaved by botulinum neurotoxin-A, however VAMP are involved in this process and they can be cleaved by botulinum neurotoxin-B introduced by incubation in low ionic strength medium.

According to the invention, obesity can be treated by inducing the light chains of clostridial neurotoxin to translocate through adipose cell membranes when the extracellular fluid is acidified (clostridial neurotoxin cannot penetrate adipose membranes under normal extracellular conditions).

In one example of this embodiment, about 5 ml of normal saline containing the light chains from 50 units of botulinum neurotoxin is injected into the abdominal adipose tissue of a 30 year old women. A stimulating electrode is passed into the target area and electrical stimulation is applied as the needle is passed multiple times parallel to the skin, about 1 cm deep. The electrical stimulation causes and acidic environment at its tip. In this manner, the adipocytes that were adjacent to the needle tip throughout its movements experience a momentary acidification, thereby effecting translocation of the botulinum neurotoxin light chains. After entering the adipose cells, the light chains block vesicular activity thereby preventing significant glucose uptake. The adipocytes metabolize their own fat stores and slowly shrink in size. The result is a shrinking of the volume of adipose tissue in the area and a enhanced cosmetic appearance. The use of lytic toxins from anthrax, diptheria, and others can be used to cause lysis of the cells and remove them permanently.

The sympathetic system controls fat metabolism in adipocytes to some extent, perhaps through special receptors such the beta 3 receptor. Thus, another example of this embodiment of the invention. Injection of tetanus neurotoxin raises the sympathetic tone and promote utilization of lipid stores. Therefore, injection of 10 units of tetanus neurotoxin in 5 ml of saline into the subcutaneous abdominal fat causes it to decrease in size even without acid mediated translocation.

8.5 Viral Infection

In yet another embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to treat, reduce the symptoms of, and/or prevent viral infections in mammals.

Viral infections can be treated with regulated SNARE inhibitors, for example, an upper respiratory tract infection or "common cold". Viral infection of the nasal mucosa causes inflammation manifested as congestion, primary and neurogenic inflammation. These cases last a matter of days, and according to the invention, can be treated with the botulinum neurotoxin E or its light chain, or its light chain in a amphipathic protein conjugate with the botulinum neurotoxin C2II.

Botulinum neurotoxins C2 is not a neurotoxin, it is composed of 2 chains, C2II is the larger chain and contains the binding and translocating domains. C2I is the toxic chain that exhibits depolymerizing action. Actin is needed for cellular skeleton movement and secretion of certain vesicles. C2II binds to cells and then is joined by C2I, which begins the endosomal internalization stage. The essential part of C2I that allows it to bind to C2II are the first 250 amino acids of its N-terminal. If these same binding fragments are covalently bound to another toxin, it will also be translocated into cells by the C2II. Among the cells that C2 binds with are the mast cells, which mediate much of the inflammatory and allergic reactions within nasal mucosa. For example, see U.S. Pat. No. 6,429,189 (issued Aug. 10, 2002), hereby incorporated herein by reference, which discloses cytotoxin (non-neurotoxin) for the treatment of human headache disorders and inflammatory diseases.

In one example of this embodiment of the invention, a 50 year old man with a cold is treated by spraying into each nasal cavity 30 units of botulinum neurotoxin C2II/E hybrid. The congestion and excessive mucoid production improve for the following 3 days.

In another example, the same patient is treated with 20 units of botulinum neurotoxin B in 2 ml saline placed on cotton pledgets, which are placed onto each turbinate for one hour.

8.6 Cancer

In one embodiment of the invention, therapeutically effective amounts of regulated SNARE inhibitors are administered locally, preferably by way of acid mediated translocation, protein transduction domains, or encapsulation vectors—so as to increase or facilitate cell membrane translocation and/or binding—to treat, reduce the symptoms of, and/or prevent cancer in mammals.

The methods of the invention are useful for benign or malignant tumors, sarcomas (originating from mesenchymal cells), carcinomas (originating from epithelial cells), or mixed or compound tumors. Sarcomas include those from connective, endothelial, hematopoietic and muscle cells. (fi squamous cell carcinoma, basal cell carcinoma, adenocarcinoma, bladder cancer, glioblastoma, gliomas, astrocytoma, oligodendroglioma, breast, neuroendocrine, cholangiosarcoma, colorectal, head and neck, hepatocellular, chronic lymphocytic leukemia, acute myeloid leukemia, non-small cell lung carcinoma, mesothelioma, non-Hodgkin's lymphoma, cutaneous B-lymphoma, cutaneous T-cell lymphoma, melanoma, multiple myeloma, myeloproliferative disease, myelodysplastic syndromes, ovarian, pancreatic, prostatic, renal cell carcinoma, and soft tissue sarcoma.

Cancer involves inappropriate cell function, most importantly cell growth. Part of the disturbed metabolism of cancer cells is the loss of control over certain aspects of vesicle trafficking. Recent research has identified that many proteins associated with the control of regulated exocytosis and/or vesicle fusion in general are expressed at abnormal levels,. Most importantly, some of these proteins are the SNARE isoforms cleaved by regulated SNARE inhibitors. See e.g., *A Fusion Inhibitor On Endosomes*, The Journal of Cell Biology (2003) 162:125-137, hereby incorporated herein by reference; Sun W et al., *Hrs regulates early endosome fusion by inhibiting formation of an endosomal SNARE complex*, The Journal of Cell Biology (2003) 162: 125-137, hereby incorporated herein by reference; Chan A et al. *A Putative Link Between Exocytosis And Tumor Development*, Cancer Cell (2002) 6:427-8, hereby incorporated herein by reference; Palmer R et al., *Induction Of BAIAP3 By The EWS-WTI chimeric Fusion Implicates Regulated Exocytosis In Tumorigenesis*, Cancer Cell (2002) 6:497-505), hereby incorporated herein by reference.

Many pharmaceuticals can impair cancer cell growth but are unable to be used in vivo as they cannot be selectively targeted to cancer cells. However, the clostridial neurotoxins are unusual in that the particular SNARE isoforms that they neutralize are not essential for normal cell survival. Surprisingly, genetic experiments that selectively eliminate either SNAP-25, (see e.g., Washbourne P et al., *Genetic Ablation Of The T-SNARE SNAP-25 Distinguishes Mechanisms Of Neuroexocytosis*, Nature Neuroscience (2002) 5:19-26, hereby incorporated herein by reference), or VAMP-2, (Schoch S et al., *SNARE Function Analyzed in Synaptobrevin/VAMP Knockout Mice*, Science (2001) 294, hereby incorporated herein by reference) in mice come to term with normal brain and body morphology. Of course the fetuses are still born because all neurotransmission is blocked, including the muscles of respiration. However, the fact that all cells grow and differentiate normally shows that SNAP 25 and VAMP 2 are not critical for normal cell survival.

According to the invention, clostridial neurotoxins can impair cancer cell growth by interfering with vesicle trafficking. While not wanting to be bound by any theory, it appears that the unregulated growth of cancer requires inappropriate use of regulated exocytosis pathways. Therefore, interference with these pathways inhibits the growth and may cause cancer cell death. Therefore the use of regulated SNARE inhibitors either alone or by combination of multiple types of may be of increased benefit in certain types of cancer. Specifically combination of SNAP-25 inhibitors (botulinum neurotoxins/A, C, E and IgA protease) may be used with VAMP-2 inhibitors (botulinum neurotoxins/B, F, G, H, and tetanus toxin). Also according to the invention, if clostridial neurotoxins is introduced, the cells in a local area of the body that contain cancer cells, only the cancer cells will be impaired, although of course nerve function in the area will also be blocked.

Botulinum type C1 has some special features that make it a particularly useful therapeutic for cancer, botulinum neurotoxin/C1 cleaves syntaxin 1 which is one of the core proteins in the SNARE mechanism (See e.g., Foran P et al., *Botulinum Neurotoxin C1 Cleaves Both Syntaxin And Snap-25 In Uintact And Permeabilized Chromaffin Cells: Correlation With Its Blockade Of Catecholamine Release*, Biochemistry (1996) 35:2630-2636, hereby incorporated herein by reference; Williamson et al.: Mal. Biol. Cell 6:61a, 1995, hereby incorporated herein by reference; J. Biol. Chem. 271:7694-7699, 1996, hereby incorporated herein by reference). However, recent work has shown that syntaxin 1 has a second role in cells. Specifically, syntaxin 1 is necessary for cell division (See e.g., Conner S & Wessel G M: *Syntaxin Is Required for Cell Division* Molecular Biology of the Cell, Vol. 10, 2735-2743, August 1999, *Syntaxin and 25-kDa synaptosomal-associated protein: Differential effects of botulinum neurotoxins C1 and A on neuronal survival*, hereby incorporated by reference). In Drosophila embryos, syntaxin 1 is necessary for vesicle trafficking at an early stage of embryogenesis. Without syntaxin 1 embryos stop growing at a very early stage as cell division is impaired (Burgess R et al., *The Synaptic Protein Syntaxin* 1 *Is Required for Cellularization of Drosophila Embryos*, The Journal of Cell Biology, Volume 138, Number 4, Aug. 25, 1997 861-875, hereby incorporated herein by reference).

Normally, chemotherapeutic agents that stop cell division have extremely toxic side effects, in fact this is the basis for many of the worst side effects of cancer chemotherapy. However, botulinum neurotoxin C1 injected locally does not appear to have any deleterious effects in humans (Eleopra R, *Botulinum neurotoxin serotypes A and C do not affect motor units survival in humans: an electrophysiological study by motor units counting* Clinical Neurophysiology 113 (2002) 1258-1264, hereby incorporated herein by reference). In fact, clinical trials of botulinum neurotoxin/C1 injection into muscle have been done for the purposes of evaluating it as a substitute for botulinum neurotoxinlA and no toxic side effects have been reported (Eleopra R et al., *Botulinum neurotoxin serotype C: a novel effective botulinum toxin therapy in human*, Neuroscience Letters 224 (1997) 91-94), hereby incorporated herein by reference).

According to the invention, botulinum neurotoxin C1 stops cell division and is therefore be of great value in cancer therapy, but does not have any toxic effects when injected locally into humans. Syntaxin 1 fragment (which is cleaved by botulinum toxin C1) is one of the regulated SNARE proteins. But is has been very recently discovered that syntaxin 1 is necessary for cell division. Within muscle tissue there no toxic effect due to cell division inhibition because muscle cells are mature, but cancer is a disease where cell division is out of control. Thus, inhibitors of syntaxin 1, such as botulinum toxin C1 are useful to treat cancer.

Clostridial neurotoxins normally do not enter into non-neural cells therefore it is unclear how they could be used as therapeutic agents. However, this invention discloses multiple methods of introducing proteins into cells. According to the invention, clostridial neurotoxins and other regulated SNARE inhibitors can be delivered to all cells in a tissue area with technology that has been well known in the art. Therefore, this embodiment of the invention combines a fortuitous combination of disparate elements to provide a method of treating cancer.

In one example of this aspect of the invention, a forty-year-old female has squamous cell carcinoma of the lung. A balloon catheter is threaded through the femoral artery to the branch of the pulmonary artery supplying the lung lobe containing the tumor. The balloon is inflated thereby occluding the artery and stopping circulation. One cc of a saline solution containing 20 units of wild type botulinum toxin C1 are infused in conjunction with 10 cc of physiological solution buffered to pH 4.5. The solutions thereby are delivered through out the distribution of the artery that includes the lung cancer. By the action of the acidic pH the light chains of botulinum C1 translocate into the cytoplasm of the cancer cells. After ten minutes slight suction is applied to the catheter to retrieve any excess botulinum neurotoxin/C1 so that it does not spread systemically when blood flow is restored. The balloon catheter is deflated and normal blood flow is restored. The catheter is removed and the patient is observed overnight and then discharged from the hospital. Two weeks later she returns for a CT scan of the chest to evaluate the change in the tumor size.

In another embodiment of the above example, 20 units of botulinum neurotoxin/A are mixed with 20 units of botulinum neurotoxin/B. In another embodiment of the above example 40 units of *Clostridia botulinum* A are used.

In another embodiment of the above example, 100 units of Botulinum toxin light chains are used in substitution for the whole toxin. The unit measure of light chain is the molar equivalent of a unit of whole toxin, i.e., the same number of molecules are present in each case. The pH for direct translocation of light chains is lower than the whole toxin, preferably about pH 4.0. To ensure that in vivo tissue buffers do not interfere with the method, a slightly lower buffered pH of 3.8 is used in the toxin solution. In this example suction is not necessary to retrieve the light chains as they cannot enter any other cells in the body and will be metabolized and excreted.

In another example, a fifty-year-old male with prostate cancer whose primary cancer has been resected has a metastatic lesion in the left femur. A long bone biopsy needle is placed through the skin and into the marrow of the femur and 10 ml of acidic solution buffered to pH 4.5 are infused in conjunction with 20 units of botulinum neurotoxin A.

In another example a patient has a squamous cell carcinoma of the left vocal fold. The patient is anesthetized and a laryngoscope is inserted to allow the clinician to directly visualize the tumor. One tenth of a cc of viscous gel containing 100 units of botulinum C1 light chain is applied onto the lesion.

8.7 Fever

In one embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to treat, reduce the symptoms of, and/or fever.

Abdominal processes that induce fever do so by way of the vagal branch to the liver. Sectioning that branch or chemodenervating it eliminates fever. This is valuable in many clinical conditions, however, the problem is selective delivery of drugs to the liver. The liver receives all of the venous flow from the GI tract via the portal circulation. One of the areas that drain into this system is the venous system above the anal sphincter, known as the source for hemorrhoids.

According to this embodiment of the invention, a speculum or similar device can be positioned in the anus so as to compress possible communication of the portal venous system with the remaining systemic system. Clostridial neurotoxin is injected directly into this venous area to be distributed to the liver.

In one example of this embodiment, a 30-year-old male with abdominal Hodgkin's disease and fever undergoes an injection of 30 units of botulinum neurotoxin to the venous rectal area. The botulinum neurotoxin is circulated to the liver where it binds and blocks autonomic neurons thereby stopping the signals for fever. Those skilled in the art can readily appreciate that what is disclosed is a method of delivering pharmaceuticals to the liver without significant systemic spread. This same technique can be used for a variety of pharmaceuticals and gene therapy agents.

8.8 Skin Disorders

Skin disorders are best discussed together as the barrier function of the skin is a special technical problem for drug delivery. The skin covers the external surface of the body and its outer layer, the stratum corneum, is a non-viable water impermeable barrier composed of dead keratinocytes. The only openings in this barrier are areas at which hair follicles emerge, which simultaneously are where sebum glands are located, and the sweat ducts.

8.9 Sweating, Eccrine and Apocrine

In one embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to treat, reduce the symptoms of, and/or prevent conditions associated with eccrine and apocrine sweating.

Eccrine sweat glands are present throughout skin and produce the thin, watery secretion known as sweat. These glands are under cholinergic control and are blocked by transcutaneous injections of either botulinum toxin A or B. Injections in each axilla require approximately 100 units of botulinum toxin A or 2000 units of botulinum toxin B. With either toxin the decrease in sweating lasts four months or longer (Dressler D et al, *Botulinum toxin type B for treatment of axillar hyperhidrosis* J Neurol. 2002 December; 249(12):1729-32). Apocrine sweat glands are mostly present in the axilla and genital area and produce a special sweat that has lipid and protein components. In the presence of moisture from eccrine glands, apocrine sweat is broken down by bacteria to produce a body odor. Botulinum neurotoxin injections into axilla block this body odor (see, e.g., Heckmann M et al., *Amelioration of body odor after intracutaneous axillary injection of botulinum toxin A*. Arch Dermatol. 2003 January 139(1):57-9), hereby incorporated herein by reference. U.S. patent application publication 2002/0086036A1, hereby incorporated herein by reference, teaches methods for treating hyperhidrosis and U.S. Pat. No. 5,766,605 (issued Jun. 16, 1998), hereby incorporated herein by reference, teaches treatment of autonomic nerve dysfunction with botulinum toxin.

Despite the success of botulinum toxin injections a major drawback is the need for multiple transcutaneous needle injections that are perceived as extremely painful. Therefore, there is a need for a non-injected, local delivery mechanism for the treatment of hyperhidrosis.

In one example of this embodiment of the invention, a forty-year-old female complains of excessive sweating and odor from her axilla. A warm moist towel is placed over her axilla to open the sweat pores for ten minutes. Then 1 cc of a normal saline solution containing a regulated SNARE inhibitor is placed over 5 $cm^2$ of the axillary skin corresponding to the area containing sweat pores. The regulated SNARE inhibitor may between 1 to 100 units botulinum type A, and preferably 10-50 units, and most preferably 30 units; or between 1 and 4000 units botulinum B, preferably 20-2000 units, and most preferably 1000 units; or 1-4000 units tetanus neurotoxin, preferably 10-1000 units, and most preferably 500 units; or between 1 and 1000 units of light chain from botulinum toxin A, B, C, D, E, F, or G or tetanus toxin, preferable between 10 and 500 units and most preferably between 50 and 200 units). An 5 $cm^2$ square electrode with an oxidized iridium surface is placed over the axillary skin corresponding to the area containing sweat glands, a distant second electrode of between 1 and 20 $cm^2$ of surface area is placed on the outside of the ipsilateral arm. Direct current is passed between the electrodes with the axillary electrode being the anode. Current ranges from 0.1 to 10 mAmp, preferably 10-500 mAmp, most preferably 20-100 mAmp. Current is applied for 10 seconds to 20 minutes, preferably 1 minute to 10 minutes, most preferably 3-6 minutes. While not wanting to be bound by theory the regulated SNARE inhibitors diffuse down the sweat ducts and are made hydrophilic upon production of an acidic pH produced by the direct current flow. The light chains are then translocated into the sweat gland cells and their surrounding nerve supply.

In another embodiment of this invention the same patient is treated with a regulated SNARE inhibitor encapsulated into liposomes. A 1 cc solution of liposomes is placed onto the 5 $cm^2$ axillary skin containing the sweat pores. The liposomes contain 1-5000 units of IgA protease, preferably 50 to 3000 units, most preferably 500-1000 units; or 1-1000 units of botulinum A light chain, preferably 10-500 units, or more preferably 100-200 units.

In another embodiment of this invention, the same patient is treated with a mixture of regulated SNARE inhibitor and a protein transduction domain.

8.11 Disease Associated with Holocrine Secretions

In one embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to treat, reduce the symptoms of, and/or prevent disease associated with holocrine secretions and acne.

Holocrine glands produce sebum. All hair follicles have sebum producing glands that empty into the area of the hair shaft. Excessive production of sebum can lead to infections of the follicle resulting in a pimple or furuncle. Sebum is at least partly under the control of substance P secreting nerves and blocking these nerves decreases sebum production.

8.11 Disease Related to Mucus Secretion

In another embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to treat, reduce the symptoms of, and/or prevent disease related to mucous secretion.

Excessive mucous secretion is one of the symptoms of asthma, COPD and cystic fibrosis, and rhinitis in the nose and mucoid otitis media in the ear. Acid mediated translocation allows control over these processes indirectly by their innervation and directly by translocation into secreting cells.

In one example of this embodiment of the invention, a forty-year-old female complains of excessive sweating and odor from her axilla. A warm moist towel is placed over her axilla to open the sweat pores for ten minutes. Then 1 cc of a normal saline solution containing a regulated SNARE inhibitor is placed over 5 $cm^2$ of the axillary skin corresponding to the area containing sweat pores. The regulated SNARE inhibitor can be between 1 to 100 units of botulinum type A, and preferably 10-50 units, and most preferably 30 units; or between 1 and 4000 units botulinum B, preferably 20-2000 units, and most preferably 1000 units; or 1-4000 units tetanus neurotoxin, preferably 10-1000 units, and most preferably 500 units; or between 1 and 1000 units of light chain from botulinum toxin A, B, C, D, E, F, or G or tetanus toxin, preferable between 10 and 500 units and most preferably between 50 and 200 units). An 5 $cm^2$ square electrode with an oxidized iridium surface is placed over the axillary skin corresponding to the area containing sweat glands, a distant second electrode of between 1 and 20 $cm^2$ of surface area is placed on the outside of the ipsilateral arm. Direct current is passed between the electrodes with the axillary electrode being the anode. Current ranges from 0.1 to 10 mAmp, preferably 10-500 mAmp, most preferably 20-100 mAmp. Current is applied for 10 seconds to 20 minutes, preferably 1 minute to 10 minutes, most preferably 3-6 minutes. While not wanting to be bound by theory the regulated SNARE inhibitors diffuse down the sweat ducts and are made hydrophilic upon production of an acidic pH produced by the direct current flow. The light chains are then translocated into the sweat gland cells and their surrounding nerve supply.

8.12 Prostatic Hypertrophy

In one embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to treat, reduce the symptoms of, and/or prevent prostatic hypertrophy.

Prostatic hypertrophy is frequent in males over fifty and causes difficulty urinating due to partial obstruction to urinary flow. Denervation is known to cause involution of the glandular elements of the prostate and shrink the gland. Botulinum neurotoxin A has been shown to shrink the gland in rodents.

In one example of this embodiment, a 25-gauge needle is inserted through the perineum of a 60-year-old male with prostatic hypertrophy under ultrasound guidance. In succession the following solutions are injected, 5 ml 1% lidocaine with epinephrine, then 5 ml of 40 units of botulinum neurotoxin A in saline, then 5 ml of acidic solution. The botulinum neurotoxin light chains are translocated into the glandular elements as well as the innervating neurons. Involution of the gland is noted by one week and the patient is free of obstruction for six months.

8.13 Disease Treatable by Gene Therapy

In still one more embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to treat, reduce the symptoms of, and/or prevent disease that are treatable by gene therapy.

An amphipathic protein with cargo molecule coding for the membrane transporter of cystic fibrosis is injected via a bronchoscope to one lobe of the lung followed by injection of an acidic solution of pH 4.5. The gene enters the secretory cells and the mucus consistency decreases to normal. The procedure is repeated every month for each lobe until the disease is controlled.

8.14 Disease of the Veins: Venous Stasis, Varicose Veins, Hemorrhoids

In still yet another embodiment of the invention, therapeutically effective amounts of regulated SNARE inhibitors are administered locally to treat, reduce the symptoms of, and/or prevent disease of the veins, such as venous stasis, varicose veins, and hemorrhoids.

Veins are high compliance low-pressure vessels. With aging, they become weaker resulting in dilatation manifest as varicose veins in the subcutaneous tissue and hemorrhoids around the anal sphincter. Deeper veins can allow blood to stagnate and clot causing deep venous thrombosis and pulmonary emboli. Vein contraction is adrenergic therefore increasing the sympathetic tone causes contraction and relieves many of these conditions. In addition, sympathetic nerves are unregulated with increasing NGF.

In one example of this embodiment of the invention, a 60-year-old female suffers from varicose veins on the back of her hands that are cosmetically undesirable. About 5 units of tetanus neurotoxin in a 5 ml solution is administered by percutaneous injection around the veins. A week later the tetanus neurotoxin has been transported retrograde and causes increased sympathetic tone to the veins. They in turn constrict and become smaller and less noticeable.

In another example of this embodiment, a fifty-year-old female has varicose veins in her legs. She has 5 IU of tetanus toxoid injected around the veins. The sympathetic neurons increase in size and the varicose veins shrink.

In another example, a 60-year-old male with hemorrhoids is treated by administering an anal suppository containing 5 units of tetanus neurotoxin in a rapid degradable gelatin. After an hour he expels the suppository. In one week the sympathetic tone to the hemorrhoids has increased and they shrink.

In still another example, a solution containing a hybrid tetanus neurotoxin suspended in normal saline is administered to the nose of a thirty-year-old male suffering from a viral URI (cold) with nasal congestion. The tetanus neurotoxin has had its light chain replaced by that from botulinum neurotoxin E, whose duration of action is one day. The next day the sympathetic activity to the venous cavities of the nasal mucosa increases and their size shrinks thereby relieving his nasal congestion for a day. Application of botulinum neurotoxin E could also be done to decrease rhinorrhea and neurogenic inflammation.

In yet another example, a combination of botulinum neurotoxin, a cholinergic blocker, with tetanus neurotoxin, a cholinergic (that is blocked) and adrenergic agonist is administered for beneficial effect greater then can be achieved by each alone. The parasympathetic and sympathetic nervous system often innervate and have opposite effects on the same organ.

8.15 High Blood Pressure

In still yet another embodiment of the invention of the invention, therapeutically effective amounts of regulated SNARE inhibitors are administered locally to treat, reduce the symptoms of, and/or prevent high blood pressure.

In animals, injection of tetanus neurotoxin into the anterior stomach wall produces decreased blood pressure. Presumably this is due to its transport through the vagus to the nucleus ambiguus where it can diffuse to the neighboring external formation where cardiovascular control neurons are present. This is another example of using the circuitry of the CNS to effect a target indirectly.

In an example of this embodiment of the invention, a fifty-year-old black male with severe hypertension undergoes fiberoptic laparoscopy where a 1 week biodegradable pellet containing 5 units of tetanus neurotoxin is injected into the anterior stomach wall. The tetanus neurotoxin is transported retrograde to the brainstem and the patient's blood pressure decreases for three months.

8.16 Use Regulated SNARE Inhibitors Simultaneously as a Therapeutic Agent and as a Vaccine In another embodiment of the invention, therapeutically effective amounts of regulated SNARE inhibitors are administered locally, preferably, by way of acid mediated translocation, protein transduction domains, or encapsulation vectors—so as to increase or facilitate cell membrane translocation and/or binding—to act simultaneously as a therapeutic agent and as a Vaccine.

Most humans and farm animals are vaccinated against tetanus neurotoxin, in fact, the vaccine is the largest biopharmaceutical product in the world. Instead of separate vaccinations of toxoid and therapeutic applications of tetanus neurotoxin, tetanus neurotoxin can be used for both. Especially in farm animals a single injection of slow release would have the therapeutic effect while still vaccinating the animal.

In an example of this embodiment of the invention, 200 units of tetanus neurotoxin in a 2 month biodegradable microparticle is injected into the tail of a cow. The tetanus neurotoxin is slowly released and is transported retrograde. As the amount is in excess of what the projection neurons from the tail can absorb, the remainder diffuses into the CSF or is transported retrograde to cause general motor disinhibition, that is widespread increases in muscle tone to increase meat production, while simultaneous causing vaccination. This example also demonstrates that tetanus neurotoxin can be used to cause disinhibition in second or third order projection neurons.

CONCLUSION

From the above summary, description and examples, it is clear that in certain embodiments, the invention relates to:

In one embodiment, the invention relates to a methods and compositions for modulating cellular function in a mammal comprising locally administering a modulatorily effective amount of a regulated SNARE inhibitor and a translocating agent to the mammal, whereby translocation of the regulated SNARE inhibitor is facilitated.

In another embodiment, the invention relates to methods and compositions for modulating cellular function in a mammal comprising locally administering an modulatorily effective amount of a regulated SNARE inhibitor to the mammal at a selected site and decreasing a pH value at the selected site.

In yet another embodiment, the invention relates to methods and compositions for modulating cellular function in a mammal comprising locally administering an modulatorily effective amount of a regulated SNARE inhibitor to the mammal at a selected site, by way of a protein transduction domain.

In still another embodiment, the invention relates to methods and compositions for modulating cellular function in a mammal comprising locally administering an modulatorily effective amount of a regulated SNARE inhibitor to the mammal at a selected site, by way of an encapsulation vector.

In one more embodiment, the invention relates to methods and compositions for modulating cellular function of a mammal suffering from a disease or medical condition, whereby the disease or medical condition is treated.

In still yet another embodiment, the invention relates to methods and compositions for modulating cellular function of a mammal suffering from a disease or medical condition comprising locally administering a therapeutically effective amount of a regulated SNARE inhibitor to a mammal in need of such treatment at a selected site and decreasing a pH value at the selected site.

In another embodiment, the invention relates to methods and compositions for modulating cellular function of a mammal suffering from a disease, malfunction, or dysfunction comprising locally administering a therapeutically effective amount of a regulated SNARE inhibitor to a mammal in need of such treatment at a selected site by way of a protein transduction domain.

In a further embodiment, the invention relates to methods and compositions modulating cellular function of a mammal suffering from a disease, malfunction, or dysfunction comprising locally administering a therapeutically effective amount of a regulated SNARE inhibitor to a mammal in need of such treatment at a selected site by way of an encapsulation vector.

In another embodiment, the invention relates to pharmaceutical formulations for modulating cellular function in a mammal comprising a therapeutically effective amount of a regulated SNARE inhibitor and a translocating agent in a pharmaceutically acceptable carrier for local delivery. Preferably, the translocating agent is an acid, an acidic environment, an encapsulating vector, or a transduction domain and the regulated SNARE inhibitor is a bacterial neurotoxin.

In yet a further embodiment, the invention relates to the use of a regulated SNARE inhibitors in the preparation of a medicament for a method of treating a disease or medical condition in a mammal comprising locally administering a therapeutically effective amount of a regulated SNARE inhibitor to a mammal in need of such treatment at a selected site related to the disease, by way of acid mediated translocation, a protein transduction domain, or an encapsulation vector.

The present invention is not to be limited in scope by the specific embodiments disclosed in the examples, which are intended as illustrations of a few aspects of the invention. Any embodiments that are functionally equivalent are within the scope of this invention. Indeed, various modifications of the invention in addition to those shown and described herein will become apparent to those skilled in the art and are intended to fall within the scope of the appended claims. All cited references are hereby incorporated herein in their entireties by reference.

What is claimed is:

1. A method of treating headache pain in a mammal in need thereof comprising administering a therapeutically effective amount of a botulinum neurotoxin to treat headache pain into the mammal's pterygopalatine space, thereby blocking the mammal's sphenopalatine ganglion.

2. The method of claim 1, wherein the botulinum neurotoxin is administered by injection.

3. The method of claim 1, wherein the botulinum neurotoxin is selected from the group consisting of botulinum neurotoxin serotypes A, B, C1, D, E, F or G.

4. The method of claim 3, wherein the botulinum neurotoxin is botulinum neurotoxin serotype A.

5. The method of claim 1, wherein said administering step comprises the steps of passing a needle about 1.5 inches through the sphenopalatine canal and injecting the botulinum neurotoxin into the mammal's pterygopalatine space.

6. The method of claim 1, wherein said headache pain is associated with a migraine headache, cervicogenic headache, sinusitis, or tension headache.

7. The method of claim 1, wherein the botulinum neurotoxin is administered at a dosage of between about 0.1 units to about 1000 units.

8. The method of claim 1, wherein the botulinum neurotoxin is administered at a dosage of between about 1 unit to about 100 units.

9. The method of claim 1, wherein the botulinum neurotoxin is administered by way of acid mediated translocation, protein transduction domains, or encapsulation vectors.

10. A method of treating headache pain in a mammal in need thereof comprising administering a therapeutically effective amount of botulinum neurotoxin serotype A to treat headache pain into the mammal's pterygopalatine space, thereby blocking the mammal's sphenopalatine ganglion.

11. The method of claim 10, wherein said headache pain is associated with a migraine headache, cervicogenic headache, or tension headache.

12. The method of claim 10, wherein said administering step comprises the steps of passing a needle about 1.5 inches through the sphenopalatine canal and injecting the botulinum neurotoxin serotype A into the mammal's pterygopalatine space.

13. The method of claim 10, wherein the botulinum neurotoxin serotype A is administered at a dosage of between about 0.1 units to about 1000 units.

14. The method of claim 10, wherein the botulinum neurotoxin serotype A is administered at a dosage of between about 1 unit to about 100 units.

15. The method of claim 10, wherein the botulinum neurotoxin serotype A is administered by way of acid mediated translocation, protein transduction domains, or encapsulation vectors.

* * * * *